(12) United States Patent
Malanoski et al.

(10) Patent No.: US 7,668,664 B2
(45) Date of Patent: Feb. 23, 2010

(54) DESIGN AND SELECTION OF GENETIC TARGETS FOR SEQUENCE RESOLVED ORGANISM DETECTION AND IDENTIFICATION

(75) Inventors: Anthony P. Malanoski, Greenbelt, MD (US); Zheng Wang, Burke, VA (US); Baochuan Lin, Bethesda, MD (US); David A Stenger, Herndon, VA (US); Joel M Schnur, Burke, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 282 days.

(21) Appl. No.: 11/843,126
(22) Filed: Aug. 22, 2007

(65) Prior Publication Data

US 2008/0033706 A1     Feb. 7, 2008

Related U.S. Application Data

(63) Continuation-in-part of application No. 11/177,647, filed on Jul. 2, 2005, and a continuation-in-part of application No. 11/177,646, filed on Jul. 2, 2005, now abandoned, and a continuation-in-part of application No. 11/268,373, filed on Nov. 7, 2005, and a continuation-in-part of application No. 11/422,425, filed on Jun. 6, 2006, and a continuation-in-part of application No. 11/559,513, filed on Nov. 14, 2006, and a continuation-in-part of application No. 11/422,431, filed on Jun. 6, 2006, now Pat. No. 7,623,997.

(60) Provisional application No. 60/823,510, filed on Aug. 25, 2006, provisional application No. 60/823,101, filed on Aug. 22, 2006, provisional application No. 60/743,639, filed on Mar. 22, 2006, provisional application No. 60/735,824, filed on Nov. 14, 2005, provisional application No. 60/735,876, filed on Nov. 14, 2005, provisional application No. 60/691,768, filed on Jun. 16, 2005, provisional application No. 60/626,500, filed on Nov. 5, 2004, provisional application No. 60/590,931, filed on Jul. 2, 2004, provisional application No. 60/609,918, filed on Sep. 15, 2004, provisional application No. 60/631,437, filed on Nov. 29, 2004, provisional application No. 60/631,460, filed on Nov. 29, 2004.

(51) Int. Cl.
  *G01N 33/48* (2006.01)

(52) U.S. Cl. .......................... 702/20; 702/33; 702/179; 703/2; 703/11; 706/13; 706/48; 707/3; 707/6; 435/6; 435/287.2; 435/288.4

(58) Field of Classification Search ...................... None
  See application file for complete search history.

(56) References Cited

U.S. PATENT DOCUMENTS

2003/0228599 A1   12/2003   Straus
2005/0227222 A1   10/2005   Braun et al.

OTHER PUBLICATIONS

Cleland et al., "Development of rationally designed nucleic acid signatures for microbial pathogens" *Expert Rev Mol Diagn*, 4, 303-315 (2004).
Fitch et al., "Rapid development of nucleic acid diagnostics" *Proceedings of the IEEE*, 90, 1708-1721 (2002).
Gardner et al., "Draft versus finished sequence data for DNA and protein diagnostic signature development" *Nucleic Acids Res*, 33, 5838-5850 (2005).
Herold et al., "Oligo Design: a computer program for development of probes for oligonucleotide microarrays" *Biotechniques*, 35, 1216-1221 (2003).
Lin et al., "Broad-spectrum respiratory tract pathogen identification using resequencing DNA microarrays" *Genome Research*, 16(4), 527-535 (2006).
Lin et al., "Use of Oligonucleotide Microarrays for Rapid Detection and Serotyping of Acute Respiratory Disease-Associated Adenoviruses" *J, Clin, Microbiol.*, 42(7), 3232-3239 (2004).
Malanoski et al., "Automated identification of multiple micro-organisms from resequencing DNA microarrays" *Nucleic Acids Res*, 34, 5300-5311 (2006).
Matveeva et al., "Thermodynamic calculations and statistical correlations for oligo-probes design" *Nucleic Acids Res*, 31, 4211-4217 (2003).
Mehlmann et al., "Robust sequence selection method used to develop the FluChip diagnostic microarray for influenza virus"*J Clin Microbiol*, 44, 2857-2862 (2006).
Rychlik et al., "A computer program for choosing optimal oligonucleotides for filter hybridization, sequencing and in vitro amplification of DNA" *Nucleic Acids Res*, 17, 8543-8551 (1989).
Santalucia, "A unified view of polymer, dumbbell, and oligonucleotide DNA nearest-neighbor thermodynamics" *Proc. Natl. Acad. Sci. U S A*, 95, 1460-1465 (1998).
Santalucia et al., "The thermodynamics of DNA structural motifs" *Annu. Rev. Biophys. Biomol. Struct.*, 33, 415-440 (2004).
Wang et al., "Identifying Influenza Viruses with Resequencing Microarrays" *Emerging Infectious Diseases*, 12(4), 638-646 (2006).
Wu et al., "Sequence dependence of cross-hybridization on short oligo microarrays" *Nucleic Acids Res*, 33, e84 (2005).
Zhang et al., "A model of molecular interactions on short oligonucleotide microarrays" *Nat Biotechnol*, 21, 818-821 (2003).
Counterpart PCT Search Report and Written Opinion.

*Primary Examiner*—Carolyn L. Smith
(74) *Attorney, Agent, or Firm*—John J. Karasek; Joseph T. Grunkemeyer

(57) ABSTRACT

A computer-implemented method as follows. Providing a list of target sequences associated with one or more organisms. Providing a list of candidate prototype sequences suspected of hybridizing to one or more of the target sequences. Generating a collection of probes corresponding to each candidate prototype sequence, each collection of probes having a set of probes for every subsequence. The sets consist of the corresponding subsequence and every variation of the corresponding subsequence formed by varying a center nucleotide of the corresponding subsequence. Generating a set of fragments corresponding to each target sequence. Calculating the binding free energy of each fragment with a perfect complimentary sequence of the fragment. Determining which extended fragments are perfect matches to any of the probes. Assembling a base call sequence corresponding to each candidate prototype sequence.

12 Claims, 7 Drawing Sheets

| | | |
|---|---|---|
| NOMINAL TARGET | 1 | TGTCGACAG |
| TARGETS | 10 | TGTCGACAG |
| | 20 | TGTCTCCAC |
| | 30 | TGCCGAGAG |
| | 40 | TATGGACGA |
| CANDIDATE PROTYPES | 100 | TGTCGACAG |
| | 200 | TGTCTCCAC |
| | 300 | TGCCGAGAG |
| | 400 | TATGGACGA |

*Fig. 5*

PROBES

| | | | | | | | |
|---|---|---|---|---|---|---|---|
| 111 | TGTCGAC | 211 | TGTCTCC | 311 | TGCCGAG | 411 | TATGGAC |
| 112 | TGTAGAC | 212 | TGTATCC | 312 | TGCAGAG | 412 | TATAGAC |
| 113 | TGTTGAC | 213 | TGTTTCC | 313 | TGCTGAG | 413 | TATTGAC |
| 114 | TGTGGAC | 214 | TGTGTCC | 314 | TGCGGAG | 414 | TATCGAC |
| | | | | | | | |
| 121 | GTCGACA | 221 | GTCTCCA | 321 | GCCGAGA | 421 | ATGGACG |
| 122 | GTCAACA | 222 | GTCACCA | 322 | GCCAAGA | 422 | ATGAACG |
| 123 | GTCTACA | 223 | GTCCCCA | 323 | GCCTAGA | 423 | ATGTACG |
| 124 | GTCCACA | 224 | GTCGCCA | 324 | GCCCAGA | 424 | ATGCACG |
| | | | | | | | |
| 131 | TCGACAG | 231 | TCTCCAC | 331 | CCGAGAG | 431 | TGGACGA |
| 132 | TCGTCAG | 232 | TCTACAC | 332 | CCGTGAG | 432 | TGGTCGA |
| 133 | TCGCCAG | 233 | TCTTCAC | 333 | CCGCGAG | 433 | TGGCCGA |
| 134 | TCGGCAG | 234 | TCTGCAC | 334 | CCGGGAG | 434 | TGGGCGA |

*Fig. 6*

FRAGMENTS

| | | | | | | | |
|---|---|---|---|---|---|---|---|
| 11 | TGTC | 21 | TGTC | 31 | TGCC | 41 | TATG |
| 12 | GTCG | 22 | GTCT | 32 | GCCG | 42 | ATGG |
| 13 | TCGA | 23 | TCTC | 33 | CCGA | 43 | TGGA |
| 14 | CGAC | 24 | CTCC | 34 | CGAG | 44 | GGAC |
| 15 | GACA | 25 | TCCA | 35 | GAGA | 45 | GACG |
| 16 | ACAG | 26 | CCAC | 36 | AGAG | 46 | ACGA |

EXTENDED FRAGMENTS

| | | | | | | | |
|---|---|---|---|---|---|---|---|
| 11' | TGTC | 21' | TGTCT | 31' | TGCCG | 41' | TATG |
| 12' | GTCGA | 22' | GTCT | 32' | GCCG | 42' | ATGG |
| 13' | TCGAC | 23' | TCTC | 33' | CCGA | 43' | TGGACG |
| 14' | CGACAG | 24' | CTCCA | 34' | CGAG | 44' | GGACG |
| 15' | GACA | 25' | TCCA | 35' | GAGA | 45' | GACG |
| 16' | ACAG | 26' | CCAC | 36' | AGAG | 46' | ACGA |

*Fig. 7*

| PROBE | FRAGMENT | FRAGMENT | FRAGMENT | FRAGMENT |
|---|---|---|---|---|
| 111 TGTCGAC | 11' TGTC | 12' GTCGA | 13' TCGAC | |
| 121 GTCGACA | 12' GTCGA | 13' TCGAC | 15' GACA | |
| 123 GTCTACA | 22' GTCT | | | |
| 124 GTCCACA | 25' TCCA | 26' CCAC | | |
| 131 TCGACAG | 13' TCGAC | 14' CGACAG | 15' GACA | 16' ACAG |
| 211 TGTCTCC | 11' TGTC | 21' TGTCT | 22' GTCT | 23' TCTC |
| 221 GTCTCCA | 22' GTCT | 23' TCTC | 24' CTCCA | 25' TCCA |
| 231 TCTCCAC | 23' TCTC | 24' CTCCA | 25' TCCA | 26' CCAC |
| 311 TGCCGAG | 31' TGCCG | 32' GCCG | 33' CCGA | 34' CGAG |
| 312 TGCAGAG | 36' AGAG | | | |
| 321 GCCGAGA | 32' GCCG | 33' CCGA | 34' CGAG | 35' GAGA |
| 331 CCGAGAG | 33' CCGA | 34' CGAG | 35' GAGA | 36' AGAG |
| 333 CCGCGAG | 34' CGAG | | | |
| 411 TATGGAC | 41' TATG | 42' ATGG | | |
| 421 ATGGACG | 42' ATGG | 43' TGGACG | 44' GGACG | 45' GACG |
| 431 TGGACGA | 43' TGGACG | 44' GGACG | 45' GACG | 46' ACGA |
| 432 TGGTCGA | 12' GTCGA | | | |
| 433 TGGCCGA | 32' GCCG | 33' CCGA | | |

*Fig. 8*

| CANDIDATE PROTOTYPE | | PROBE SET | BASE CALL | PROBE SET | BASE CALL | PROBE SET | BASE CALL | BASE CALL SEQUENCE |
|---|---|---|---|---|---|---|---|---|
| 100 | TGTCGACAG | 111-114 | C | 121-124 | N | 131-134 | A | CNA |
| 200 | TGTCTCCAC | 211-214 | C | 221-224 | T | 231-234 | C | CTC |
| 300 | TGCCGAGAG | 311-314 | N | 321-324 | G | 331-334 | N | NGN |
| 400 | TATGGACGA | 411-414 | G | 421-424 | G | 431-434 | N | GGN |

*Fig. 9*

| CANDIDATE PROTOTYPE | BASE CALL SEQUENCE | MATCHING ORGANISMS | | | | |
|---|---|---|---|---|---|---|
| | | A | B | C | D | E |
| 100 | CNA | | | X | X | |
| 200 | CTC | | | X | X | |
| 300 | NGN | | | | | |
| 400 | GGN | X | X | | | X |

| CANDIDATE PROTOTYPES | FINAL PROTOTYPES | ORGANISMS |
|---|---|---|
| 100 | | A |
| 200 | | B |
| 300 | | C |
| 400 | | D |
| | | E |

| CANDIDATE PROTOTYPES | FINAL PROTOTYPES | ORGANISMS |
|---|---|---|
| 100 | 400 | C |
| 200 | | D |
| 300 | | |

| CANDIDATE PROTOTYPES | FINAL PROTOTYPES | ORGANISMS |
|---|---|---|
| 200 | 400 | |
| 300 | 100 | |

*Fig. 10*

SEQUENCE LISTING

<160> NUMBER OF SEQ ID NOS: 51

<210> SEQ ID NO 1
<211> LENGTH: 101
<212> TYPE: DNA
<213> ORGANISM: Artificial
<220> FEATURE:
<223> OTHER INFORMATION: Constructed from Human adenovirus type 4
      AF542122 with modifications.  Final section (actcgccct
      cacttttaaa c) is artificial

<400> SEQUENCE: 1
ctacacgctg gccgtgggcg acaaccgtgt gctggacatg gccagcacct attttgacat     60
ccgcggcgtg ctggaccggg gactcgccct cacttttaaa c                        101

<210> SEQ ID NO 2
<211> LENGTH: 101
<212> TYPE: DNA
<213> ORGANISM: Artificial
<220> FEATURE:
<223> OTHER INFORMATION: Constructed from Human adenovirus type 5
      AF542130.1 with modifications.  Final section (actcggcct
      cacttttaag c) is artificial

<400> SEQUENCE: 2
gttcacccta gctgtgggtg ataaccgtgt gctggacatg gcttccacgt cctttgacat     60
ccgcggcgtg ctggacaggg gactcggcct cacttttaag c                        101

<210> SEQ ID NO 3
<211> LENGTH: 101
<212> TYPE: DNA
<213> ORGANISM: Artificial
<220> FEATURE:
<223> OTHER INFORMATION: Constructed by model
<220> FEATURE:
<221> NAME/KEY: misc_feature
<222> LOCATION: (1)..(101)
<223> OTHER INFORMATION: n is a, t, c, or g

<400> SEQUENCE: 3
nnnnnnnnnn nnnnnnnnnn ntaaccgtgt gctggacatg gctnnnnnnn nctttgacat     60
ccgcggcgtg ctggacannn nnnnngnnn nnnnnnnnng n                         101

<210> SEQ ID NO 4
<211> LENGTH: 101
<212> TYPE: DNA
<213> ORGANISM: Artificial
<220> FEATURE:
<223> OTHER INFORMATION: Constructed by model
<220> FEATURE:
<221> NAME/KEY: misc_feature
<222> LOCATION: (1)..(101)
<223> OTHER INFORMATION: n is a, t, c, or g

<400> SEQUENCE: 4
nnnnnnnnnn nnnnnnnnnn ntnaccgtgt gctggacatg gnnnnnnnnn nnnttgacat     60
ccgcggcgtg ctgganannn nnnnngnnn nnnnnnnng n                          101

<210> SEQ ID NO 5
<211> LENGTH: 101
<212> TYPE: DNA
<213> ORGANISM: Artificial
<220> FEATURE:
<223> OTHER INFORMATION: Constructed by model

```
<220> FEATURE:
<221> NAME/KEY: misc_feature
<222> LOCATION: (1)..(101)
<223> OTHER INFORMATION: n is a, t, c, or g

<400> SEQUENCE: 5
nnnnnnnnnn nnnnnnnnnn ntnnccgtgt gctggacatg nnnnnnnnnn nnnntgacat      60
ccgcggcgtg ctggnnannn nnnnngnnn nnnnnnnnnn n                          101

<210> SEQ ID NO 6
<211> LENGTH: 101
<212> TYPE: DNA
<213> ORGANISM: Artificial
<220> FEATURE:
<223> OTHER INFORMATION: Constructed by model
<220> FEATURE:
<221> NAME/KEY: misc_feature
<222> LOCATION: (1)..(101)
<223> OTHER INFORMATION: n is a, t, c, or g

<400> SEQUENCE: 6
nnnnnnnnnn nnnnnnnnnn nnnnnngtgt gctggacann nnnnnnnnnn nnnnnnacat      60
ccgcggcgtg ctnnnnannn nnnnngnnn nnnnnnnnnn n                          101

<210> SEQ ID NO 7
<211> LENGTH: 101
<212> TYPE: DNA
<213> ORGANISM: Artificial
<220> FEATURE:
<223> OTHER INFORMATION: Constructed by model
<220> FEATURE:
<221> NAME/KEY: misc_feature
<222> LOCATION: (1)..(101)
<223> OTHER INFORMATION: n is a, t, c, or g

<400> SEQUENCE: 7
nnnnnnnnnn nnnnnnnnnn nnnnnnnngt gctggannnn nnnnnnnnnn nnnnnnnnat      60
ccgcggcgtg nnnnnnannn nnnnngnnn nnnnnnnnnn n                          101

<210> SEQ ID NO 8
<211> LENGTH: 101
<212> TYPE: DNA
<213> ORGANISM: Artificial
<220> FEATURE:
<223> OTHER INFORMATION: Constructed by model
<220> FEATURE:
<221> NAME/KEY: misc_feature
<222> LOCATION: (1)..(101)
<223> OTHER INFORMATION: n is a, t, c, or g

<400> SEQUENCE: 8
nnnnnnnnnn nnnnnnnnnn nnnnnnnnnn nnnnnnnnnn nnnnnnnnnn nnnnnnnnnn      60
ccgcggcgnn nnnnnnannn nnnnngnnn nnnnnnnnnn n                          101

<210> SEQ ID NO 9
<211> LENGTH: 101
<212> TYPE: DNA
<213> ORGANISM: Artificial
<220> FEATURE:
<223> OTHER INFORMATION: Constructed by model
<220> FEATURE:
<221> NAME/KEY: misc_feature
<222> LOCATION: (1)..(101)
<223> OTHER INFORMATION: n is a, t, c, or g

<400> SEQUENCE: 9
```

```
nnnnnnnnnn nnnnnnnnnn nnnnnnnnnn nnnnnnnnnn nnnnnnnnnn nnnnnnnnnn        60
nngcggnnnn nnnnnnnnnn nnnnnnnnnn nnnnnnnnnn n                            101
```

<210> SEQ ID NO 10
<211> LENGTH: 112
<212> TYPE: DNA
<213> ORGANISM: Artificial
<220> FEATURE:
<223> OTHER INFORMATION: Readout from chip
<220> FEATURE:
<221> NAME/KEY: misc_feature
<222> LOCATION: (1)..(112)
<223> OTHER INFORMATION: n is a, t, c, or g

<400> SEQUENCE: 10

```
accnnnnnnn nntngnnntg ntgntgnttn catggtgcaa aantctgggn nnacaggnnc        60
annnnnnnnn nnnnnnggna tttnnnngnc tnananantg tggtgcgnan gt                112
```

<210> SEQ ID NO 11
<211> LENGTH: 112
<212> TYPE: DNA
<213> ORGANISM: Artificial
<220> FEATURE:
<223> OTHER INFORMATION: Constructed by model
<220> FEATURE:
<221> NAME/KEY: misc_feature
<222> LOCATION: (1)..(112)
<223> OTHER INFORMATION: n is a, t, c, or g

<400> SEQUENCE: 11

```
nnnnnnnnnt nntnnaattg ttgttgatta catggtgcaa aantctggga aaacaggaac        60
aannnnnnnn caaagaggta tnnnannnnn nnnnnnannn nnnnnnnnaa gt                112
```

<210> SEQ ID NO 12
<211> LENGTH: 112
<212> TYPE: DNA
<213> ORGANISM: Influenza B virus (B/Parma/4/04)

<400> SEQUENCE: 12

```
accacaaagt ggtagaattg ttgttgatta catggtgcaa aaatctggga aaacaggaac        60
aattacttat caaagaggta ttttattgcc tcaaaaagtg tggtgcgcaa gt                112
```

<210> SEQ ID NO 13
<211> LENGTH: 112
<212> TYPE: DNA
<213> ORGANISM: Influenza B virus (B/Canberra/5/97)

<400> SEQUENCE: 13

```
accacaaagc ggcagaattg ttgttgatta catggtgcaa aaacctggga aaacaggaac        60
aattgtctat caaagaggta ttttgttgcc tcaaaaggtg tggtgcgcga gt                112
```

<210> SEQ ID NO 14
<211> LENGTH: 500
<212> TYPE: DNA
<213> ORGANISM: Adenovirus 7

<400> SEQUENCE: 14

```
ttcctgccac aggagattat ctccagtgag accgggatcg aaatactgga gtttgtggta        60 aatacccctaa tgggagacga cccggaaccg ccagtgcagc ctttcgatcc acctacgctg      120
cacgatctgt atgatttaga ggtagacggg cctgaggatc ccaatgagga agctgtgaat       180 gggttttttta ctgattctat gctgctagct gccgatgaag gattggacat aaaccctcct     240
```

```
cctgagaccc ttgttacccc aggggtggtt gtggaaagcg gcagaggtgg gaaaaaattg      300
cctgatctgg gagcagctga atggacttg cgttgttatg aagagggttt tcctccgagt       360
gatgatgaag atggggaaac tgagcagtcc atccataccg cagtgaatga gggagtaaaa      420
gctgccagcg atgttttaa gttggactgt ccggagctgc ctggacatgg ctgtaagtct       480
tgtgaatttc acaggaataa                                                  500
```

<210> SEQ ID NO 15
<211> LENGTH: 700
<212> TYPE: DNA
<213> ORGANISM: Adenovirus 7

<400> SEQUENCE: 15

```
ccagcacatt ctttgacatt aggggggtgc ttgatagagg tcctagcttc aagccatatt      60
ccggcacagc ttacaattca ctggctccta agggcgcgcc taacacatct cagtggatag     120
ttacaacggg agaagacaat gccaccacat acacatttgg cattgcttcc acgaagggag     180
acaatattac taaggaaggt ttagaaattg gaaagacat tactcagac aacaagccca       240 tttatgccga taaacatat cagccagagc ctcaagttgg agaagaatca tggactgata      300
ttgatggaac aaatgaaaaa tttggaggta gagctcttaa accagctact aaaatgaagc     360
catgctacgg gtcttttgca agacctacaa acataaaagg gggccaagct aaaaacagaa     420
aagtaacacc aaccgaagga gatgttgaag ctgaggagcc agatattgat atggaatttt    480
tcgatggtag agaagctgct gacgcttttt cgcctgaaat tgtgctttac acggaaaatg    540
tcaatttgga aactccagac agccatgtgg tatacaagcc aggaacttct gatggtaact    600
ctcatgcaaa tttgggtcaa caagccatgc ctaacagacc caattacatt ggcttcaggg    660
ataactttgt aggtcttatg tactacaaca gtactggaaa                          700
```

<210> SEQ ID NO 16
<211> LENGTH: 500
<212> TYPE: DNA
<213> ORGANISM: Adenovirus 7

<400> SEQUENCE: 16

```
atggctttac acaaagccca gacggagttc ttactttaaa atgtttaacc ccactaacaa      60
ccacaggcgg gtctctacag ttaaaagtgg agggggtct acaatagat gacaccgacg        120 gttttttgaa agaaaacata agtgccacca caccactcgt taagactggt cactctatag     180
gtttgtcgct aggacccgga ttaggaacaa atgaaaacaa actttgtgcc aaattgggag     240
aaggacttac attcaattcc aacaacattt gcattaatga caatattaac acccatgga     300 caggagttaa ccccaccaga gccaactgtc aaataatggc ctccagtgaa tctaatgatt     360
gcaaattaat tctaacacta gttaaaactg gagccctcgt cactgcattt gtttatgtta     420
taggagtatc taacgatttt aatatgctaa ctacacataa aaatataaat ttcactgcag     480
agctgttttt tgattctact                                                 500
```

<210> SEQ ID NO 17
<211> LENGTH: 579
<212> TYPE: DNA
<213> ORGANISM: Adenovirus 17

<400> SEQUENCE: 17

```
atgagacacc tgcgcctcct gcctggaact gtgcccttgg acatggccgc attattgctg      60
```

| | |
|---|---:|
| gatgactttg tgagtacagt attggaggat gaactgcaac caactccgtt cgagctggga | 120 |
| cccacacttc aggacctcta tgatttggag gtagatgccc aggaggacga cccgaacgaa | 180 |
| gatgctgtga atttaatatt tccagaatct ctgattcttc aggctgacat agccagcgaa | 240 |
| gctctaccta ctccacttca tactccaact ctgtcaccca tacctgaatt ggaagaggag | 300 |
| gacgagttag acctccggtg ttatgaggaa ggttttcctc ccagcgattc agaggacgaa | 360 |
| cagggtgagc agagcatggc tctaatctca gactatgctt gtgtggttgt ggaagagcat | 420 |
| tttgtgttgg acaatcctga ggtgcccggg caaggctgta atcctgcca gtaccaccgg | 480 |
| gataagaccg agacacgaa cgcctcctgt gctctgtgtt acatgaaaaa gaacttcagc | 540 |
| tttatttaca gtaagtggag tgaatgtgag agaggctga | 579 |

<210> SEQ ID NO 18
<211> LENGTH: 692
<212> TYPE: DNA
<213> ORGANISM: Adenovirus 17

<400> SEQUENCE: 18

| | |
|---|---:|
| cttcagcctg ggcaacaagt ttaggaaccc cacggtggcc ccgacccacg atgtgaccac | 60 |
| ggaccggtcc cagcgtctga cgctgcgctt tgtgcccgtg gatcgcgagg acaccagtac | 120 |
| tcgtacaagg cgcgcttcac tctggccgtg ggcgacaacc gggtgctaga catgccagc | 180 |
| acgtactttg acatccgcgg cgtcctggac cgcggtccca gtttcaaacc ctactcgggc | 240 |
| acggcttaca cagccttgc ccccaagggc gctcccaatc ccagtcagtg ggttgccaaa | 300 |
| gaaaatggtc agggaactga taagacacat acttatggct cagctgccat gggaggaagc | 360 |
| aacatcacca ttgaaggttt agtaattgga actgatgaaa aagctgagga tggcaaaaaa | 420 |
| gatattttg caaataaact ttatcagcca gaacctcaag taggtgaaga aaactggcaa | 480 |
| gagtctgaag ccttctatgg aggcagagct cttaagaaag acacaaaaat gaagccctgc | 540 |
| tatggctcat ttgcaagacc taccaatgaa aaaggcggac aagctaaatt taagccagtg | 600 |
| gaagaggggc agcaacctaa agattatgac atagatttgg ctttctttga cacacctgga | 660 |
| ggcaccatca caggaggcac agacgaagaa ta | 692 |

<210> SEQ ID NO 19
<211> LENGTH: 529
<212> TYPE: DNA
<213> ORGANISM: Adenovirus 17

<400> SEQUENCE: 19

| | |
|---|---:|
| tcctgtcact caaactggct gacccaatca ccatagccaa tggtgatgtc tcactcaagg | 60 |
| tgggaggggg acttactttg caagaaggaa gtatgactgt agaccctaag gctcccttgc | 120 |
| aacttgcaaa caataaaaaa cttgagcttg tttatgttga tccatttgag gttagtgcca | 180 |
| ataaacttag tttaaaagta ggacatggat taaaatatt agatgacaaa agtgctggag | 240 |
| ggttgaaaga tttaattggc aaacttgtgg ttttaacagg gaaaggaata ggcactgaaa | 300 |
| atttgcaaaa tacagatggt agcagcgag gaattggtat aagtgtaaga gcaagagaag | 360 |
| ggttaacatt tgacaatgat ggatacttgg tagcatggaa cccaaagtat gacacgcgca | 420 |
| cactttggac aacaccagac acatctccta attgcaggat tgataaggag aaggattcaa | 480 |
| aactcacttt ggtacttaca aagtgtggaa gtcaaatatt agctaatgt | 529 |

<210> SEQ ID NO 20
<211> LENGTH: 609

<212> TYPE: DNA
<213> ORGANISM: Adenovirus 2

<400> SEQUENCE: 20

```
gatttagacg tgacggcccc cgaagatccc aacgaggagg cggtttcgca gattttccc      60
gagtctgtaa tgttggcggt gcaggaaggg attgacttat tcacttttcc gccggcgccc    120
ggttctccgg agccgcctca cctttccgg cagcccgagc agccggagca gagagccttg    180
ggtccggttt ctatgccaaa ccttgtgccg gaggtgatcg atcttacctg ccacgaggct    240
ggcttcccac ccagtgacga cgaggatgaa gagggtgagg agtttgtgtt agattatgtg    300
gagcacccccg ggcacggttg caggtcttgt cattatcacc ggaggaatac gggggaccca    360
gatattatgt gttcgctttg ctatatgagg acctgtggca tgtttgtcta cagtaagtga    420
aaattatggg cagtcggtga tagagtggtg ggtttggtgt ggtaattttt ttttaatttt    480
tacagttttg tggtttaaag aattttgtat tgtgattttt taaaaggtcc tgtgtctgaa    540
cctgagcctg agcccgagcc agaaccggag cctgcaagac ctacccggcg tcctaaattg    600
gtgcctgct                                                           609
```

<210> SEQ ID NO 21
<211> LENGTH: 700
<212> TYPE: DNA
<213> ORGANISM: Adenovirus 2

<400> SEQUENCE: 21

```
agtggtctta catgcacatc tcgggccagg acgcctcgga gtacctgagc cccgggctgg     60
tgcagtttgc ccgcgccacc gagacgtact tcagcctgaa taacaagttt agaaacccca    120
cggtggcacc tacgcacgac gtaaccacag accggtccca gcgtttgacg ctgcggttca    180
tccctgtgga ccgcgaggat accgcgtact cgtacaaagc gcggttcacc ctggctgtgg    240
gtgacaaccg tgtgcttgat atggcttcca cgtactttga catccgcggc gtgctggaca    300
gggggcctac ttttaagccc tactccggca ctgcctacaa cgctctagct cccaagggcg    360
ctcctaactc ctgtgagtgg gaacaaaccg aagatagcgg ccgggcagtt gccgaggatg    420
aagaagagga agatgaagat gaagaagagg aagaagaaga gcaaaacgct cgagatcagg    480
ctactaagaa aacacatgtc tatgcccagg ctccttttgtc tggagaaaca attacaaaaa    540
gcgggctaca aataggatca gacaatgcag aaacacaagc taaacctgta tacgcagatc    600
cttcctatca accagaacct caaattggcg aatctcagtg gaacgaagct gatgctaatg    660
cggcaggagg gagagtgctt aaaaaaacaa ctcccatgaa                         700
```

<210> SEQ ID NO 22
<211> LENGTH: 500
<212> TYPE: DNA
<213> ORGANISM: Adenovirus 2

<400> SEQUENCE: 22

```
atagctataa atgcaggaaa gggtctggag tttgatacaa acacatctga gtctccagat     60
atcaacccaa taaaaactaa aattggctct ggcattgatt acaatgaaaa cggtgccatg    120
attactaaac ttggagcggg tttaagcttt gacaactcag gggccattac aataggaaac    180
aaaaatgatg acaaacttac cctgtggaca accccagacc catctcctaa ctgcagaatt    240
cattcagata tgactgcaa atttactttg gttcttacaa aatgtgggag tcaagtacta    300
gctactgtag ctgctttggc tgtatctgga gatctttcat ccatgacagg caccgttgca    360
```

```
agtgttagta tattccttag atttgaccaa aacggtgttc taatggagaa ctcctcactt    420
aaaaaacatt actggaactt tagaaatggg aactcaacta atgcaaatcc atacacaaat    480
gcagttggat ttatgcctaa                                                500

<210> SEQ ID NO 23
<211> LENGTH: 500
<212> TYPE: DNA
<213> ORGANISM: Adenovirus 4

<400> SEQUENCE: 23
atgaggcacc tgagagacct gcccgatgag aaaattatta tcgcttccgg gagcgagatt     60
ctggaactgg tggtaaatgc tataatgggc gacgaccatc cggaaccccc caccccattt    120
gagacacctt cgctgcacga tttgtatgat ctggaggtgg atgtgcccga ggacgacccc    180
aacgaggagg cggtaaatga tttatttagc gatgccgcgc tgctagctgc cgaggaggct    240
ttaagcccta gacacggcag aggtgataaa aagatcccct ggcttaaagg ggaagagatg    300
gacttgcatt gctatgagga atgcttgccc ccgagcgatg atgagtacga gcaggcgatc    360
cagaacgcag cgagccaggg agtgcaagcc gccagcgaga ctttgcact ggactgccca    420 cctttgcccg gacacggctg taagtcttgt gaatttcatc gtatgaatac tggagataaa    480
gctgtgttat gtgcactttg                                                500

<210> SEQ ID NO 24
<211> LENGTH: 722
<212> TYPE: DNA
<213> ORGANISM: Adenovirus 4

<400> SEQUENCE: 24
atggccaccc catcgatgct gccccagtgg gcgtacatgc acatcgccgg acaggacgct     60
tcggagtacc tcagtccggg tctggtgcag ttcgcccgcg ccacagacac ctacttcagt    120
ctggggaaca agtttagaaa ccccacggtg gcgcctaccc acgatgtgac caccgaccgc    180
agccagcggc tgacgctgcg cttcgtgccc gtggaccggg aggacaacac ctactcgtac    240
aaagtgcgct acacgctggc cgtgggcgac aaccgtgtgc tggacatggc cagcacctac    300
tttgacatcc gcggcgtgct ggaccggggc cctagcttta acccctactc cggcactgcc    360
tacaacagtc tggctcccaa gggagcgccc aatacctgcc agtggaagga tgctaacagc    420
aaaatgcata cctttggggt agctgccatg ccaggtgtta ctgggaaaaa gatagaagct    480
gatgggctgc ctattagaat agattcaact tctggaactg acacagtaat ttatgctgat    540
aaaactttcc aaccagaacc acaagttgga aatgacagtt gggttgacac caatgatgca    600
gaggaaaaat atggaggcag agctctaaag gacactacaa atatgaaacc ctgctatggt    660
tcattcgcca agcctaccaa caaagaaggt gggcaggcta acttaaaaga ttcagaaacc    720
gc                                                                   722

<210> SEQ ID NO 25
<211> LENGTH: 500
<212> TYPE: DNA
<213> ORGANISM: Adenovirus 4

<400> SEQUENCE: 25
acgcaccgac catgcccttc atcaaccctc ccttcgtctc ttcagatgga ttccaagaaa     60
agcccctggg ggtgttgtcc cttaggctgg ccgaccctgt caccaccaag aatggggaaa    120
tcaccctcaa tctgggggag ggggtggacc ttgacgactc gggaaaactc attgcaaaca    180
```

-continued

```
cagtcaacaa ggccattgcc cctcttagtt tttccaacaa caccatttcc cttaacatgg      240
atacccattt atacaccaaa gatggaaaac tatccttaca agtttctcca ccattaagta      300
tattaagatc aacaattcta aatacattag ctctagcttt tggctcaggt ttaggactgc      360
gtggcagcgc tctggcagta cagttagcct ctccacttac atttgatgat aaagggaata      420
taaagattac cctaaatagg ggattgcatg ttacaacagg aaatgcaatt gaaagcaaca      480
ttagttgggc taaaggtata                                                  500
```

<210> SEQ ID NO 26
<211> LENGTH: 720
<212> TYPE: DNA
<213> ORGANISM: Coxsackievirus A8

<400> SEQUENCE: 26

```
cagggcccaa tgggcgtcag cactctggta ccgaggtacc tttgtgcgcc tgttttattt       60
cccctttccc tgatgcaact tagaagctcc gaactaatga tcaatagtag gtgtggcacg      120
ccagccacat cttgatcaag cacttctgtt tacccggacc gagtatcaat aagctgcgca      180
agcggctgaa ggagaaagcg ttcgttatcc ggccaactac ttcgagaagc ttagtaccac      240
catgaacgtt gcagagtgtt tcgttcagca aaccccggt gtagatcagg ccgatgagtc       300
accgcgttcc ccatgggcga ccatggcggt ggctgcgttg gcggcctgcc catggagcaa      360
tccatgggac gctctaatac tgacatggtg cgaagagcct attgagctag ttggtgatcc      420
tccggcccct gaatgcggct aatcctaact gcggagcatg cgcccacaag ccagtgggtg      480
gtgtgtcgta acgggtaact ctgcagcgga accgactact tgggtgtcc gtgtttcctt      540 ttatctttac attggctgct tatggtgaca attgaagaat tgttaccata tagctattgg      600
attggccatc cggtgtgcaa tagagcgatt atatacctat tgttggatt tgttccattg       660 acatatagat ctcttaacac tctacaacac atcttgatct tgaacacgag aaaatggggg      720
```

<210> SEQ ID NO 27
<211> LENGTH: 500
<212> TYPE: DNA
<213> ORGANISM: Coxsackievirus A8

<400> SEQUENCE: 27

```
agaagagaga catcttggac ccaacaactc gtgatgttag caagatgaag ttttacatgg       60
acaagtacgg gctagaccta ccatactcta cttatgtcaa agatgaactc agggccatag      120
acaagatcaa gaaagggaag tctcgcctca tagaggcaag tagcctaaat gactcagtat      180
acttgaggat gacatttggg cacctttatg aagctttcca tgctaatcca ggtacaatca      240
ccggttcagc tgtcggatgc aacccagatg tgttctggag caagcttcca attctgctcc      300
cgggatcgct ttttgcattt gactactcag ggtatgatgc tagtctcagt cctgtatggt      360
ttagggcact agaaatagtc ctgcgggaaa ttggctactc agaggaagca gtgtctctta      420
tagaagggat caaccacact caccacgtgt accgcaataa aacctattgt gtactcggag      480
ggatgccctc aggctgctca                                                  500
```

<210> SEQ ID NO 28
<211> LENGTH: 720
<212> TYPE: DNA
<213> ORGANISM: Coxsackievirus B4

<400> SEQUENCE: 28

-continued

```
cagggcccaa tgggcgctag cacactggta ttccggtacc tttgtgcgcc tgttttataa     60 cccccccccca gttcgcaact tagaagcaaa gaaacaatgg tcaattactg acgcagcaac    120
ccagctgtgt tttggccaag tacttctgtg tccccggact gagtatcaat aagctgcttg    180
cgcggctgaa ggagaaaccg ttcgttaccc ggccaactac ttcgagaagc ctagtaacgc    240
catgaacgtt gaggagtgtt tcgctcagca cttcccccgt gtagttcagg tcgatgagtc    300
accgcgttcc ccacgggtga ccgtggcggt ggctgcgttg gcggcctgcc tgtggggcaa    360
cccgcaggac gctctgatac agacatggtg tgaagagcct attgagctag ttggtagtcc    420
tccggcccct gaatgcggct aatcctaact gcggagcaca cgttcgcaag ccagcgagtg    480
gtgtgtcgta acgggcaact ctgcagcgga accgagtact ttgggtgtcc gtgtttcctt    540
ttattcttac cttggctgct tatggtgaca attgaaagat tgttaccata tagctattgg    600
attggccatc cagtgtcaaa tagagcaatc atatatctgt ttgttggttt cgttcccttg    660
gactacagaa atcttaaaac tctttatttc atattgagac tcaatacgat aaaatgggag    720
```

```
<210> SEQ ID NO 29
<211> LENGTH: 500
<212> TYPE: DNA
<213> ORGANISM: Coxsackievirus B4

<400> SEQUENCE: 29
ccaaaaagac caaagacctg accaaattga aggaatgtat ggacaagtac ggattaaact     60
tgccgatggt gacatacgtg aaggatgagc ttagatcagc agagaaggtg gccaaaggga    120
aatctagact cattgaagca tccagcttga acgactctgt tgcgatgagg caaacatttg    180
gtaatttgta caaggcattc cacttaaacc cggggattgt aacgggcagt gcagtcgggt    240
gcgatccaga cgttttctgg agtaaaatac ctgtgatgct agacggacac cttatagcct    300
tcgactactc cggttatgac gccagtctga gccccgtgtg gtttgcttgt ctaaagttgc    360
tgcttgaaaa actcgggtac acacataaag agacaaacta cattgactac ttatgcaact    420
cccaccacct atacagagac aaacactact ttgtacgtgg cggtatgccc tcagggtgct    480
ctggtaccag catcttcaac                                                500
```

```
<210> SEQ ID NO 30
<211> LENGTH: 720
<212> TYPE: DNA
<213> ORGANISM: Coxsackievirus B5

<400> SEQUENCE: 30
cagggcccac tgggcgccag cactctggta tcacggtacc tttgtgcgcc tgttttaaaa     60
ccctctcccc aatttgaaac ttagaagcaa tacacctcga tcaatagtag gcatgacacg    120
ccagccatgt cttgatcaag cacttctgtt tccccggact gagtatcaat aaactgcttg    180
cgcggtcgaa ggagaaaacg tccgttaccc gactaactac ttcgagaaac ccagtaacac    240
catggaaatt gcggagtgtt tcactcagca cattcccagt gtagatcagg tcgatgagtc    300
accgcattcc ccacgggtga ccgtggcggt ggctgcgctg gcggcctgcc catggggcaa    360
cccatgggac gcttcaatat ggacatggtg tgaagagtct attgagctag ttagtagtcc    420
tccggcccct gaatgcggct aatcctaact gcggagcacg tgcctccatt ccagggggtg    480
gcgtgtcgta acgggcaact ctgcagcgga accgactact ttgggtgtcc gtgtttcttt    540
taattttata ctggctgctt atggtgacaa ttgaaagatt gttgccatat agctattgga    600
ttggccatcc ggtatccaac agagcaattg tgtacctttt tgttggattt gtaccactta    660
```

```
ccagaacaag ttttcataca ctgtgttaca ttattagact aaacacagaa aaatgggagc    720

<210> SEQ ID NO 31
<211> LENGTH: 500
<212> TYPE: DNA
<213> ORGANISM: Coxsackievirus B5

<400> SEQUENCE: 31
tctttccaaa aagaccaagg atttaaccaa gttaaaggaa tgcatggata aatatggctt     60
gaacttgcca atggtaactt atgttaaaga cgagctcagg tctgcagaga aggtagcaaa    120
agggaaatcc agattgatag aagcatccag cttgaatgac tccgtggcaa tgagacaaac    180
attcggcaac ctatacaaaa cttttcatct aaatccaggg attgtgactg gcagtgctgt    240
tgggtgtgac ccagacctct tttggagtaa ataccggtg atgttagatg gtcaccttat     300
agcctttgat tactctggat acgatgctag cttgagcccc gtctggtttg cctgcctaaa    360
actattactt gagaaacttg gatactcgca caaggagacc aattatattg attacctgtg    420
caactcccat cacctgtaca gggacaaaca ctattttgtg cggggtggca tgccttcagg    480
atgttctggc acaagtatct                                               500

<210> SEQ ID NO 32
<211> LENGTH: 720
<212> TYPE: DNA
<213> ORGANISM: Echovirus 4

<400> SEQUENCE: 32
cagggcccat tgggcgctag caccctggta ttacggtacc tttgtgcgcc tgttttatac     60
ccccatcccc aatcgaaact tagaagcatt acacactgat caataggagg cgcggcacgc    120
cagccatgcc aagatcaagc acttctgtct ccccggaccg agtatcaata gactgcttgc    180
gcggttgaag gagaaaacgt tcgttacccg gccaactact tcgagaaacc tagtaccacc    240
atgaaagttg cggagtgttt cgctcagcac taccccagtg tagatcaggc cgatgagtca    300
ccgcgttccc cacgggtgac cgtggcggtg gctgcgctgg cggcctgcct atggggcaac    360
ccataggacg ctctaataca gacatggtgt gaagagtcta ttgagctagt tggtgatcct    420
ccggcccctg aatgcggcta atcctaactg cggagcacac gctcacaagc cagtgagtgg    480
tgtgtcgtaa tgggtaactc cgcagcggaa ccgactactt tgggtgtccg tgtttccttt    540
taacttcatt ttggctgctt atggtgacaa ttaagaaatt gttaccatat agctattgga    600
ttggccatcc ggtgactagt agagctatta tatacttgtt tgttggcttt gtaccactaa    660
actataaagt ccttagaact cttgatttta tactaatttt gaataaggca aatgggagc    720

<210> SEQ ID NO 33
<211> LENGTH: 500
<212> TYPE: DNA
<213> ORGANISM: Echovirus 4

<400> SEQUENCE: 33
aaagaagacc agggacctga ccaagctgaa ggagtgcatg gacaagtatg gcctgaacct     60
gccaatggta acctatgtga aagatgaact cagatccgca gaaaaggtgg cgaagggaaa    120
atctaggctc atcgaggcgt ccagtttgaa tgactccgtg gcaatgagac aaacattcgg    180
caacctatac aaaacttttc atctaaaccc agggattgtg actggcagtg ccgtcgggtg    240
tgatccggat ctttttggga gtaaaatacc agtaatgttg gacggtcatc tcatagcctt    300
```

```
tgattattct ggatatgatg ctagcttgag tcccgtatgg tttgcttgtc taaaactact    360
acttgagaaa cttggttact cgcacaaaga gaccaattac attgactacc tgtgcaactc    420
ccatcacctg tacagggata agcattactt tgtgcggggt ggcatgccat caggatgttc    480
tggcacaagc atcttcaatt                                                500

<210> SEQ ID NO 34
<211> LENGTH: 720
<212> TYPE: DNA
<213> ORGANISM: Echovirus 11

<400> SEQUENCE: 34
cagggcccac tgggcgctag cacactggta tcacggtacc tttgtgcgcc tgttttatac     60
ccccttcccg caaccgcaaa tttagaagca aagctaaccc gatcgatagc ggatgcgcat    120
gccagccgca ttttgatcaa gtacttctgt ttccccggac cgagtatcaa tagactgctc    180
acgcggttga aggagaaaac gtccgttacc cgaccaacta cttcgagaaa cctagtaaca    240
tcatgaatgt tgcagggcgt ttcgatcagc acgaccctgg tgtagatcag gctgatgagt    300
caccgcattc cccacgggtg accgtggcgg tggctgcgtt ggcggcctgc ctatggggtg    360
acccatagga cgctctaata cggacatggt gcgaagagtc tattgagcta gttggtagtc    420
ctccggcccc tgaatgcggt taatcctaac tgccgacgac atacccctaa tccaaggggc    480
agtgtgtcgt aacgggcaac tctgcagcgg aaccgactac tttgggtgtc cgtgtttcct    540
tttattttta tactggctgc ttatggtgac aatctcagag ttgttaccat atagctattg    600
gattggccat ccggtgagca acagagctgt catttatcag tttgttggct ttatacctct    660
aaatcacacg gttttttttt tttggaacgc ttgtattcat cttaaccctc aataaggcaa    720

<210> SEQ ID NO 35
<211> LENGTH: 500
<212> TYPE: DNA
<213> ORGANISM: Echovirus 11

<400> SEQUENCE: 35
ctacccttat gttgcactag gcatcaagaa gagagacatc ctttcaagga ggaccaggga     60
tctaaccaag ttgaaggaat gtatggataa atacggtttg aacttaccga tggtgactta    120
tgtgaaagat gaacttaggt ctgcagacaa agtagcaaaa gggaagtcta ggttgattga    180
agcatccagt ttgaatgact ctgtagcaat gagacaaaca tttggcaacc tgtacagaac    240
cttccatcta aacccaggga tcgtgactgg tagcgctgtc gggtgcgacc cggacctctt    300
ttggagtaaa attccagtga tgttggatgg tcacctcata gcctttgact actctggata    360
tgatgctagc ttgagccccg tgtggtttgc ctgcctaaaa ctattacttg agaaattagg    420
ctacacacac aaggaaacaa attacattga ctacctgtgt aattcccacc acctgtacag    480
agacaaaaca tactttgagc                                                500

<210> SEQ ID NO 36
<211> LENGTH: 720
<212> TYPE: DNA
<213> ORGANISM: Echovirus 20

<400> SEQUENCE: 36
cagggcccat gggcgctag cactctggta ttacggtacc tttgtgcgcc tgttttatgt      60
cccctccccc aatcgcaact tagaagcaac acacactgat caacagtaag cgtggcatac    120
cagccacgtt ttgatcaagc acttctgtta ccccggactg agtatcaata gactgctcac    180
```

-continued

```
gcggttgaag gagaaagcgt tcgttatccg gccaactact tcgagaaacc tagtaacacc    240
gtgaaagttg cagagtgttt cgctcagcac taccccagtg tagatcaggt cgatgagtca    300
ccgcattccc cacgggcgac cgtggcggtg gctgcgctgg cggcctgcct acggggaaac    360
ccgtaggacg ctctaataca gacatggtgc gaagagtcta ttgagctagt tggtagtcct    420
ccggcccctg aatgcggcta atcctaactg cggagcacac acccccaagc caggggggcag    480
tgtgtcgtaa cgggtaactc tgcagcggaa ccgactactt tgggtgtccg tgtttcattt    540
tattcctatg ctggctgctt atggtgacaa ttgacagatt gttaccatat agctattgga    600
ttggccatcc ggtgactaat agagccatta tataccactt tgttgggttt ataccactca    660
acttgaaaga ggtcaaaaca ctacagctca tcattaaatt gaacacaaca aaatgggagc    720
```

<210> SEQ ID NO 37
<211> LENGTH: 500
<212> TYPE: DNA
<213> ORGANISM: Echovirus 20

<400> SEQUENCE: 37

```
aaagaagacc aaggacttga ctaagctaaa agagtgtatg gacaagtacg gtctcaacct     60
accaatggtg acttatgtga aagacgaact cagatctgca gagaaggtag caaagggaaa    120
atctaggctg attgaagcat ccagtttgaa tgattcagtg gctatgagac agacatttgg    180
caacctgtac aaagctttcc acctgaaccc agggattgtg actggtagtg cagttgggtg    240
cgacccagac ctcttttgga gcaaaatacc agtgatgttg gatggacatc tcatagcatt    300
tgactattct gggtatgatg ctagcttaag tcctgtctgg tttgcatgtt taaaaatgct    360
acttgagaag cttggataca cacataaaga gacaaactac attgactact tgtgcaactc    420
ccatcacctg tacagggata agcattactt tgtgaggggt ggcatgccct cagggtgttc    480
tggcaccagt atctttaact                                                500
```

<210> SEQ ID NO 38
<211> LENGTH: 720
<212> TYPE: DNA
<213> ORGANISM: Echovirus 21

<400> SEQUENCE: 38

```
cagggcccac cgggcgctag cacactggta tcgcggtacc tttgtgcgcc tgttttattt     60
accctgccct gatgtaactt agaagcatga caccaacgat caatagcagg ctcaatgcac    120
caattgggtc aagatcaagc acttctgtta ccccggactg agtatcaata agctgctagc    180
gcggctgaag gagaaaaagt tcgttacccg gccagctact tcgagaaacc tagtatcacc    240
atgaaagttg cgtggcgttt cgctccgcac aaccccagtg tagatcaggt cgatgagtca    300
ccgcattccc cacgggcgac cgtggcggtg gctgcgttgg cggcctgccc gtggagcaat    360
ccatgggacg ctataataca gacatggtgt gaagagtcta ttgagctagc tggtagtcct    420
ccggcccctg aatgcggcta atcctaactg cggagcaggt acccacgaac cagtgggcag    480
tctgtcgtaa tgggcaactc cgcagcggaa ccgactactt tgggtgtccg tgtttccttt    540
tatttcaact tggctgctta tggtgacaat tgagagattg ttaccatata gctattggat    600
tggccatccg gtgactaaca gagctatcat ataccttttt attggctttg tgccacttac    660
tctgaaagag gtcaagactc tgcattatat catactattg aatgctataa aatgggagcg    720
```

<210> SEQ ID NO 39

-continued

<211> LENGTH: 500
<212> TYPE: DNA
<213> ORGANISM: Echovirus 21

<400> SEQUENCE: 39
gctctgggta tcaagaagag agacatcctc tcaaagaaga ccagggacct gactaagctg 60
aaagagtgca tggacaagta cggcctaaac ctaccaatgg taacctacgt gaaagatgaa 120
ctcagatctg cagagaaggt ggcaaaggga aagtccaggc tcattgaggc gtccagtttg 180
aatgactccg tggcaatgag acagacattc ggcaacctat ataaaacctt tcacctaaac 240
ccagggattg tgactggcag cgccgtcggg tgtgacccgg atctcttttg gagtaaaata 300
ccagtgatgt tggacggtca cctcatagcc tttgattatt ctggatatga tgctagcttg 360
agtcccgtat ggtttgcttg tctaaaacta ctacttgaga aacttggtta ttcgcacaaa 420
gagaccaatt acattgatta cctgtgcaac tcccatcact tgtacaggga caagcattat 480
tttgtgcggg gtggcatgcc 500

<210> SEQ ID NO 40
<211> LENGTH: 720
<212> TYPE: DNA
<213> ORGANISM: Echovirus 24

<400> SEQUENCE: 40
cagggcccac agggcgctag cactctggta tcacggtacc tttgtgcgcc tgttttatta 60
ccccttcccc aattgaaaat tagaagcaat gcacaccgat caacagcagg cgtggcgcac 120
cagtcacgtc tcgatcaagc acttctgttt ccccggaccg agtatcaata gactgctcac 180
gcggttgaag gagaaagtgt tcgttatccg gctaaccact tcgagaaacc cagtaacacc 240
atgaaagttg cagggtgttt cgctcagcac ttccccagtg tagatcaggt cgatgagtca 300
ccgcgttccc cacgggcgac cgtggcggtg gctgcgttgg cggcctgcct atgggttaac 360
ccataggacg ctctaataca gacatggtgc gaagagttta ttgagctggt tagtatccct 420
ccggcccctg aatgcggcta atcctaactg cggagcacgt gcctccaatc caggggggttg 480 catgtcgtaa cgggtaactc tgcagcggaa ccgactactt tgggtgtccg tgtttccttt 540
tattcttata ctggctgctt atggtgacaa tcgaggaatt gttaccatat agctattgga 600
ttggccatcc ggtgtctaac agagcgatta tatacctctt tgttggattt atgcagctca 660
ataccaccaa ctttaacaca ttgaaatata tcttaaagtt aaacacagca aaatgggagc 720

<210> SEQ ID NO 41
<211> LENGTH: 500
<212> TYPE: DNA
<213> ORGANISM: Echovirus 24

<400> SEQUENCE: 41
ctatgtcgca ctgggtataa agaagagaga catcctctca aagaagacca aggacctgac 60
taagctaaaa gagtgcatgg ataagtatgg tttgaacctg ccgatggtga cttatgtgaa 120
agatgaactc aggtccgcag agaaggtagc aaaaggcaag tctaggctga tcgaagcatc 180
cagtttgaat gattcagtgg caatgagaca gacatttggt aatctgtaca agaccttcca 240
cctgaaccca gggattgtga ctggtagtgc agttgggtgt gacccagaca tcttttggag 300
taaaataccg gtgatgttgg atggacatct catagctttt gattactctg ggtatgatgc 360
tagcttaagt cctgtctggt ttgcttgctt aaaaatgcta cttgagaagc ttggatatac 420
acacaaagag acaaactata ttgattactt gtgcaactcc catcacctgt acagagacaa 480 gcattactttt gtgagggtg                                                        500

<210> SEQ ID NO 42
<211> LENGTH: 720
<212> TYPE: DNA
<213> ORGANISM: Echovirus 25

<400> SEQUENCE: 42
cagggcccac tgggcgctag cactctggta ctacggtacc tttgtgtgcc tgttttatac    60
ccctccccct actgaaactt agaagcaatt cataccgatc aatagtgggc gtggcacacc   120
agccgtgtct agatcaagca ctcctgtttc cccggaccga gtatcaatag actgctcacg   180
cggttgaagg agaaaacgtt cgttatccgg ctaactactt cgaaaaacct agtaacacca   240
tgaaagttgc ggagtgtttc actcagcact tccccagtgt agatcaggtc gatgagtcac   300
cgcattcctc acgggcgacc gtggcggtgg ctgcgctggc ggcctgccta tggggtgacc   360
cataggacgc tctaatacag acatggtgcg aagagtctat tgagctagtt agtagtcctc   420
cggcccctga atgcggataa tcctaactgt ggagcagata cccacgaacc agtgggcagt   480
ctgtcgtaac gggcaactcc gcagcggaac cgactacttt gggtgtccgt gtttcctttt   540
attccaaatc tggctgctta tggtgacaat tgagagattg ttgccatata gctattggat   600
tggccatccg gtgaataata gagcgataat atatttgttt gttggattcg tgccacttag   660
tctgaaagtt ttgagaacac tcaactacgt tttattgctg aatagtgcaa gatgggagct   720

<210> SEQ ID NO 43
<211> LENGTH: 500
<212> TYPE: DNA
<213> ORGANISM: Echovirus 25

<400> SEQUENCE: 43
gcgctaggca tcaagaagag agacatccta tccaagaaga ctaaagattt gaccaaactt    60
aaagaatgta tggataagta tggcttgaat ctgccaatgg taacctatgt gaaagatgag   120
ctcaggtcag ttgaaaaagt ggcgaaggga aagtccagac taattgaagc atctagtttg   180
aatgactccg tggcgatgag gcaaacattt ggcaacttgt acaaaacctt ccacttaaac   240
ccggggattg tgacaggcag tgcagttgga tgcgacccag acctcttttg gagcaaaata   300
cccgtgatgc tagatggaca cctcatagct tttgactact ccggctacga tgccagtttg   360
agccctgtat ggtttgcttg tctgaagctg ctgctcgaga agctcgggta cacacacaag   420 gagacaaaact acattgacta cctatgcaat tcccaccacc tgtatagaga taaacactac   480
ttcgtacgcg gtggtatgcc                                                500

<210> SEQ ID NO 44
<211> LENGTH: 720
<212> TYPE: DNA
<213> ORGANISM: Coxsackievirus A18

<400> SEQUENCE: 44
agaggcccac gtggcggcca gtactccggt attgcggtac ccttgtacgc ctgttttaca    60
ctcccttccc cgtaacttag acgcaataaa ccaagttcac taggagggggt gcaaaccagc   120 accaccacga acaagcactt ctgtttcccc ggtgacattg tatagactgt atccacggtt   180
gaaaacgatt gatccgttat ccgctcttgt acttcgagaa gcctagtatc atcttggaat   240
cttcgacgcg ttgcgctcag cattcaaccc cagaatgtag cttaggtcga tgagtctgga   300

-continued

```
cattcctcac cggtgacggt ggtccaggct gcgttggcgg cctacctgtg acccaaagtc    360
acaggacgct agttgtgaac aaggtgtgaa gagcctattg agctacaaga gagtcctccg    420
gcccctgaat gcggctaatc ctaaccacgg agcaagtgct cacgaaccag tgagtggctt    480
gtcgtaacga gcaattctgt ggcggaaccg actactttgg gtgtccgtgt ttccttttta    540
actttaaatg gctgcttatg gtgacaatca ttgattgtta tcataagccg aattggattg    600
gccatccggt gaaaatcaag ttgatcattt atttgtttgt tggattcact ccattaactc    660
atttttcaat tgacctaata cgtattgtat tattagttag aaacatacat cacaatgggt    720

<210> SEQ ID NO 45
<211> LENGTH: 500
<212> TYPE: DNA
<213> ORGANISM: Coxsackievirus A18

<400> SEQUENCE: 45
gccatgtatg gcactgatgg tcttgaggca ttggacctca gtactagtgc agggtaccca     60
tatgttgcta tgggaaaaaa gaaaagggat atcctcaaca aacaaaccag agataccaag    120
gagatgcaaa ggctactaga tacttatggc ataaacttac cattggtcac atatgtgaag    180
gatgagctca gatcaaaaac aaaagtagaa caaggcaaat ccaggttgat tgaagcctca    240
agtctcaatg attcagttgc catgagaatg gcatttggta atctgtatgc agcttttcat    300
aaaaacccag gagtagtcac aggctcggca gttggttgtg acccagattt gttttggagc    360
aagataccag tgttaatgga ggarrractc tttgctttcg actatacagg atatgatgct    420
tcactcagtc ctgcttggtt tgaggctctc aaaatggttc ttgagaaaat tggatttgga    480
gatagggtag attacattga                                                500

<210> SEQ ID NO 46
<211> LENGTH: 720
<212> TYPE: DNA
<213> ORGANISM: Coxsackievirus A22

<400> SEQUENCE: 46
gaggcccacg tggcggccag tactctggta ttacggtacc tttgtacgcc tgttttatat     60
cccctcccct gagtaacttt agaagcaatt caaaaggttc aatagagggg gtacaatcca    120
gtaccaccat gaacaagcac ttctgtttcc ccggtgaggc tacataaact gtacccacgg    180
ttgaaagtgg ctaatccgtt atccgctcaa gtacttcgag aagcctagta ataccttgga    240
atcttcgacg cgttgcgctc agcactctaa cccgggtgta gcttaggtcg atgagtctgg    300
gcatacccca ccggtgacgg tggcccaggc tgcgttggcg gcctacccat ggctaacgcc    360
atgggacgct agttgtgaac aaggtgtgaa gagcctattg agctacttga gagtcctccg    420
gcccctgaat gcggctaatc ctaaccacgg agcaagtgct ctcaaaccag agagtggctt    480
gtcgtaacgc gtaagtctgt ggcggaaccg actactttgg gtgtccgtgt ttccttttat    540
ttttatcatg gctgcttatg gtgacaatct aagattgtta tcatatagct tttggattgg    600
ccatccggtt gttgtttaga gcgtttcatc tgtgctttgt ttgtttgacc agatcaatat    660
aaacactaca tcctatttgt tcataatggg agctcaagtt tctactcaga aatctgggtc    720

<210> SEQ ID NO 47
<211> LENGTH: 500
<212> TYPE: DNA
<213> ORGANISM: Coxsackievirus A22

<400> SEQUENCE: 47
```

```
ttatccttat gtagctatag ggaaaaagaa aagggatatt ctcaataaac aaacaagaga    60
caccaaagaa atgcagaaaa tgctagacaa atatgggata aacctaccat tggtaaccta   120
tgttaaggat gaacttagat cgaaaacaaa ggtagaacaa gcaaatcta ggttgattga    180 agcaagttcc ctaaatgatt cagtcgccat gaggcaggct tttggtcact tgtatgctaa   240
gttccaccaa aacccaggaa taataacagg ttcagcagta ggatgtgacc cagatgtgtt   300
ttggagcaaa gtaccagtga tgttggatgg agaactcttt gcttttgact acacaggcta   360
tgatgcttca ctctccccag cctggtttga ggccttgaaa atggtgcttg agaaaattgg   420
atttggtgac agagttgatt ttatagacta cttaaaccac tcacaccact tatacaggaa   480
taaattatat tgtgtcaagg                                               500

<210> SEQ ID NO 48
<211> LENGTH: 720
<212> TYPE: DNA
<213> ORGANISM: Echovirus 70

<400> SEQUENCE: 48
agaggcccac gtggcggcta gtactccggt accccggtac ccttgtacgc ctgttttata    60 ctcccttttcc caagtaactt tagaagaaat aaactaatgt tcaacaggag ggggtacaaa   120
ccagtaccac cacgaacaca cacttctgtt tccccggtga agttgcatag actgtaccca   180
cggttgaaag cgatgaatcc gttacccgct taggtacttc gagaagccta gtatcatctt   240
ggaatcttcg atgcgttgcg atcagcactc taccccgagt gtagcttggg tcgatgagtc   300
tggacacccc acaccggcga cgtggtccag gctgcgttgg cggcctaccc atggctagca   360
ccatgggacg ctagttgtga acaaggtgcg aagagcctat tgagctacct gagagtcctc   420
cggcccctga atgcggctaa tcccaaccac ggagcaaatg ctcacaatcc agtgagtggt   480
ttgtcgtaat gcgcaagtct gtggcggaac cgactacttt gggtgtccgt gtttcctttt   540 attttttatta tggctgctta tggtgacaat ctgagattgt tatcatatag ctattggatt   600
agccatccgg tgtatctg aaattttgcc ataacttttt cacaaatcct acaacattac     660
actacacttt ctcttgaata attgagacaa ctcataatgg gagcacaagt ttctagacaa   720

<210> SEQ ID NO 49
<211> LENGTH: 500
<212> TYPE: DNA
<213> ORGANISM: Echovirus 70

<400> SEQUENCE: 49
aagaaaagag acatcttcaa cagacaaact agagatacaa cagagatgac caaaatgttg    60
gacaaatatg gtgtggattt gcccctttgtc acatttgtca aagatgaact cagaagcaga   120
gagaaagtag agaagggcaa gtctagattg attgaagcta gttcttttaaa tgattcagtt   180 gccatgcgag tggcatttgg aaacctttat gcaacattcc acaaaaatcc aggagtcgcc   240
actgggagcg ctgttggatg tgatccagat ttgttttggt ccaaaatccc agttatsttta   300 gatggaaaaa ttttttgcatt tgactacaca ggttatgatg ccagtctctc accagtctgg   360
tttgcatgcc taaagaaaac tctggtaaaa ttaggttata ctcatcaaac agcatttgtt   420
gattacttgt gtcactcggt tcacttgtac aaagacagaa aatacatagt gaacggtgga   480
atgccatcag gctcatctgg                                               500

<210> SEQ ID NO 50
```

-continued

```
<211> LENGTH: 720
<212> TYPE: DNA
<213> ORGANISM: Echovirus 68

<400> SEQUENCE: 50
agggcccacg tggcggctag tactctggta tctcggtacc tttgtacgcc tgttttaatt      60
ccctccccaa cgtaacttag aagcttttaa accaaagctc aataggtgga gcgcaaacca     120
gcgctcttat gagcaagcac ttctgtctcc ccggtgtggt tgtatagact gtccccacgg     180
ttgaaaacaa cttatccgtt aaccgctata gtacttcgag aaacctagta ttgccttcgg     240
agtgttgatg cgttgcgctc agcacactaa cccgtgtgta gcttgggtcg atgagtctgg     300
acgtacccca ctggcgacag tggtccaggc tgcgttggcg gcctactcat ggtgaaaacc     360
atgagacgct agacatgaac aaggtgtgaa gagtctattg agctgctata gagtcctccg     420
gcccctgaat gcggctaatc ctaaccatgg agcaagtgct cacaaaccag tgagttactt     480
gtcgtaacgc gcaagtccgt ggcggaaccg actactttgg gtgtccgtgt ttcacttttt     540
acttttatga ctgctaatgg tgacaattta atattgttac catttggctt gtcgaattga     600
tcacataaga tctatagttt tgttcactga tttgctttga aataatctca cctcaaaacc     660
tccagtacat aacatttaaa gagtttaaac ttatttataa caatgggagc tcaagttact     720

<210> SEQ ID NO 51
<211> LENGTH: 500
<212> TYPE: DNA
<213> ORGANISM: Echovirus 68

<400> SEQUENCE: 51
atattcaaca gacaaaccag agatactagt gagatgacaa agatgttgga aaaatacgga      60
gttgacctac ctttcgtgac tttcgtgaaa gacgagctta gatcaagaga gaaagtcgaa     120
aaggggaagt cacgcctgat tgaagccagt tccttgaacg actcagttgc catgagggtt     180
gcctttggaa atctctacgc tacatttcat aacaatccag gcacagcaac tggtagtgca     240
gttggttgtg atccagatat attctggtca aaaatcccta ttttgttaga tggagagatt     300
tttgcttttg attacactgg ttatgacgct agtttatcac cagtgtggtt tgcctgtttg     360
aaaaaggttc tgattaaatt aggttacacc caccaaacat cttttataga ttatctatgc     420
cactcagtgc atttgtacaa ggatagaaaa tatgtaatta atggtggaat gccctctggt     480
tcttcaggta ctagtatatt                                                 500
```

DESIGN AND SELECTION OF GENETIC TARGETS FOR SEQUENCE RESOLVED ORGANISM DETECTION AND IDENTIFICATION

This application claims the benefit of U.S. Provisional Patent Application Nos. 60/823,101, filed on Aug. 22, 2006 and 60/823,510, filed on Aug. 25, 2006. This application is a continuation-in-part application of U.S. patent application Ser. No. 11/177,646 filed on Jul. 2, 2005, Ser. No. 11/177,647 filed on Jul. 2, 2005, Ser. No. 11/268,373 filed on Nov. 7, 2005, Ser. No. 11/422,425 filed on Jun. 6, 2006, Ser. No. 11/422,431 filed on Jun. 6, 2006, and Ser. No. 11/559,513 filed on Nov. 14, 2006. These applications claim priority to U.S. Provisional Patent Application Nos. 60/590,931 filed on Jul. 2, 2004, 60/609,918 filed on Sep. 15, 2004, 60/626,500 filed on Nov. 5, 2004, 60/631,437 filed on Nov. 29, 2004, 60/631,460 filed on Nov. 29, 2004, 60/735,824 filed on Nov. 14, 2005, 60/735,876 filed on Nov. 14, 2005, 60/743,639 filed on Mar. 22, 2006, and 60/691,768 filed on Jun. 16, 2005. These applications and all other referenced publications and patent documents are incorporated herein by reference.

FIELD OF THE INVENTION

The invention is generally related to resequencing microarray design.

DESCRIPTION OF RELATED ART

As the prevalence of DNA based detection methods increases, it becomes more important to have in silico methods to design, test, and improve the analysis of assays. In particular, highly multiplexed pathogen detection is a growing requirement and is potentially more efficient than multiple separate tests in costs, required sample volumes, reagents, and assay time. However, the initial development, design, and validation can become logarithmically complex, costly, and time consuming. Accurate simulation models using newly available genetic sequence information for microorganisms can potentially minimize costs and time of developing these highly multiplexed assays.

The design criteria for all nucleic acid-based assays have similar global constraints. After the target organisms are chosen, methods must be employed to choose probes that will very specifically recognize only the target organism species and yet account for all of the genetic variations (i.e. strains or subtypes) within that species. In silico design methods have been developed for PCR and spotted oligonucleotide microarrays (Cleland et al. (2004) Development of rationally designed nucleic acid signatures for microbial pathogens. *Expert Rev Mol Diagn,* 4, 303-315; Gardner et al. (2005) Draft versus finished sequence data for DNA and protein diagnostic signature development. *Nucleic Acids Res,* 33, 5838-5850; Rychlik et al. (1989) A computer program for choosing optimal oligonucleotides for filter hybridization, sequencing and in vitro amplification of DNA. *Nucleic Acids Res,* 17, 8543-8551; Fitch et al. (2002) Rapid development of nucleic acid diagnostics. *Proceedings of the IEEE,* 90, 1708-1721) assays and oligonucleotide microarrays (Herold et al. (2003) Oligo Design: a computer program for development of probes for oligonucleotide microarrays. *Biotechniques,* 35, 1216-1221; Mehlmann et al. (2006) Robust sequence selection method used to develop the FluChip diagnostic microarray for influenza virus. *J Clin Microbiol,* 44, 2857-2862), with the models for each having similar requirements.

Because the potential pool of probes, targets, and interference fragments is so large, models that result in maximal target specificity with minimal computation are preferred. In typical PCR primer or oligonucleotide microarray design algorithms, the number of base matches is counted between a probe and a target or background organism sequence. If a threshold number of matches is exceeded then hybridization is assumed (Herold et al. (2003) Oligo Design: a computer program for development of probes for oligonucleotide microarrays. *Biotechniques,* 35, 1216-1221; Mehlmann et al. (2006) Robust sequence selection method used to develop the FluChip diagnostic microarray for influenza virus. *J Clin Microbiol,* 44, 2857-2862). This level of modeling is incomplete because the ultimate detection of the probe-target hybridization depends on a single signal intensity (usually fluorescence), which may not correlate with that predicted. This results in uncertainty about how effective the selected probes will be until experimental work is preformed to validate the selections and establish intensity cutoffs for hybridization events.

More detailed thermodynamic modeling and calculations have been used to better understand match-mismatch and single match microarrays and allow predictions of intensity (Matveeva et al. (2003) Thermodynamic calculations and statistical correlations for oligo-probes design. *Nucleic Acids Res,* 31, 4211-4217; Held et al. (2003) Modeling of DNA microarray data by using physical properties of hybridization. *Proc Natl Acad Sci USA,* 100, 7575-7580; Naef et al. (2003) Solving the riddle of the bright mismatches: Labeling and effective binding in oligonucleotide arrays. *Physical Review E,* 68, 011906; Zhang et al. (2003) A model of molecular interactions on short oligonucleotide microarrays. *Nat Biotechnol,* 21, 818-821; Wu et al. (2005) Sequence dependence of cross-hybridization on short oligo microarrays. *Nucleic Acids Res,* 33, e84). The modeling approaches account for several important issues such as probe attachment to the surface, and the effect of dimer formation of the fragments or loop formation depending on the base content of the fragments. Accounting for these issues when only one or two probes might hybridize with a target is relatively straightforward. However this increased detail in the model comes at a price in that the computational requirements also increase.

In contrast to simple oligonucleotide microarrays, recent work using resequencing microarrays demonstrated that they are a viable alternative to test for multiple pathogens, including co-infections, and perform detailed discrimination of closely related pathogens and/or track pathogen mutation (Wang et al. (2006) Identifying Influenza Viruses with Resequencing Microarrays. *Emerg Infect Dis,* 12, 638-646; Lin et al. (2006) Broad-spectrum respiratory tract pathogen identification using resequencing DNA microarrays. *Genome Res,* 16, 527-535). Because sets of 4 (or 8 if anti-sense is also included) short probes, where each set represents a portion of desired sequence and all the variations of the center nucleotide position, the absolute intensity of signal from a single probe becomes less important than the differential binding/intensity across the complete probe set. This information, confirmed in both the sense and antisense directions, is used only to determine that a particular base is present with high confidence. This use of overlapping probe sets is required to directly determine a target organism's nucleotide sequence, not inferentially based on single fluorescent signal intensities of presumably specific probes (Malanoski et al. (2006) Automated identification of multiple micro-organisms from resequencing DNA microarrays. *Nucleic Acids Res,* 34, 5300-5311).

A resequencing microarray's effectiveness for broad spectrum detection of various levels of organism discrimination may be dependent on the process used to select the reference or target sequences placed on the microarray. Tradeoffs in amount of space dedicated to an organism versus the level of discrimination possible must be balanced for every organism considered. In addition, when specific or semi-specific primers are used for organism enrichment the selection of these primers can affect the possible reference sequence selections.

The overall design process can be characterized as a series of steps. First, selection of organisms and desired level of discrimination for each organism and whether specific nucleic acid markers must be tested for. Second, determination from known sequence data of sequence regions to choose reference sequences from. Third, selection of reference sequences and check for possible conflicts. Fourth, primer selection. Fifth, refinements of sequence selections. The order of several of these steps can be interchanged and refinements consist of repeating several of these steps after making changes. The first step is always the selection of organisms and the desired discrimination levels of each organism which represent constraints on the design. The size of the microarray to be used specifies the other constraint placed on the design problem. It may be that no solution is possible without altering one or more of the constraints. But all subsequent steps are aimed at meeting these requirements.

SUMMARY OF THE INVENTION

The invention comprises a computer-implemented method comprising: providing a list of target sequences associated with one or more organisms in a list of organisms; providing a list of candidate prototype sequences suspected of hybridizing to one or more of the target sequences; generating a collection of probes corresponding to each candidate prototype sequence, each collection of probes comprising a set of probes for every subsequence having a predetermined, fixed subsequence length of the corresponding candidate prototype sequence, the set consisting of the corresponding subsequence and every variation of the corresponding subsequence formed by varying a center nucleotide of the corresponding subsequence; generating a set of fragments corresponding to each target sequence, each set of fragments comprising every fragment having a predetermined, fixed fragment length of the corresponding target sequence; calculating the binding free energy of each fragment with a perfect complimentary sequence of the fragment, and if any binding free energy is above a predetermined, fixed threshold, the fragment is extended one nucleotide at a time until the binding free energy is below the threshold or the fragment is the same length as the probe, generating a set of extended fragments; and determining which extended fragments are perfect matches to any of the probes; and assembling a base call sequence corresponding to each candidate prototype sequence comprising: a base call corresponding to the center nucleotide of each probe of the corresponding prototype sequence that is a perfect match to any extended fragment, but for which the other members of the set of probes containing the perfect match probe are not perfect matches to any extended fragment; and a non-base call in all other circumstances.

BRIEF DESCRIPTION OF THE DRAWINGS

A more complete appreciation of the invention will be readily obtained by reference to the following Description of the Example Embodiments and the accompanying drawings.

FIG. 5 shows a hypothetical nominal target, list of targets, and list of prototype sequences.

FIG. 6 shows a hypothetical collection of probes.

FIG. 7 shows hypothetical lists of fragments and extended fragments.

FIG. 8 shows the perfect matches between the probes and the extended fragments.

FIG. 9 shows hypothetical base call sequences.

FIG. 10 shows the matching organisms for each candidate prototype and formation of the list of final targets.

DETAILED DESCRIPTION OF EXAMPLE EMBODIMENTS

Figures 1, 2:
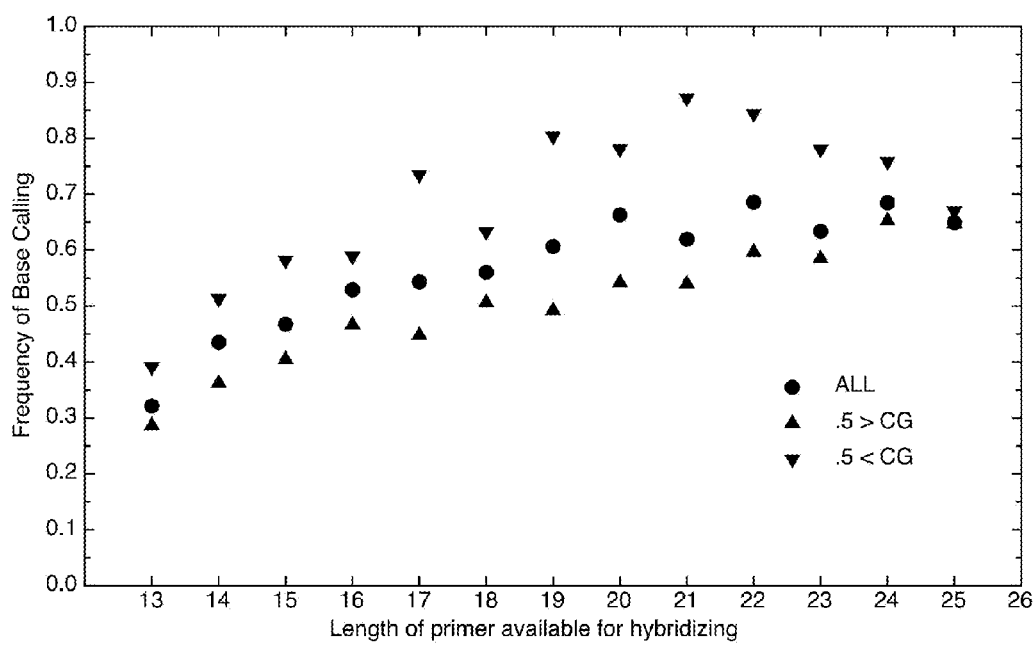
FIG. 1 shows example results of the model using different values of m from 23 to 13. A prototype sequence (used to make probe sets) and a sample sequence are shown with an asterisk above the bases that match in both sequences. Also shown are the reassembled model base call results for each probe set for different values of m. Region A has 20 contiguous bases so for m greater than 20 no probe sets in this region have matches. The longer region B has probe sets that make base calls at m=23. For each region, an increase of one or two in m results in one or two base calls at each edge to cease making base calls. These base calls depend on fragments that have more matches on one half of the probe than the other. Region C has two contiguous regions of 9 and 12 bases with a SNP in between. One probe of the SNP set has 22 bases that match in the sample but no other probe in any probe set in the region has more than 12 matching and so all are N calls at all values on N.
FIG. 2 shows the frequency of resolved base calls from primers as a function of position within the primer. ●—All, GC content: ▲—less than 50%, ▼—more than 50%.

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail.

The prevalence of DNA based detection methods, particularly for multiple pathogen detection, is evident from the volume of recently published literature. Thus, it becomes important to have in silico methods to assist in the design, initial test, and improvement of these methods as their development becomes more complex, costly, and time consuming. Recent work using resequencing microarrays demonstrates that they are a viable alternative to test for multiple pathogens, including co-infections, as well as performing detailed discrimination of closely related pathogens and/or track pathogens' genetic variations. However, the qualities of resequencing arrays require that different criteria are needed for modeling their performance at the individual probe level. In addition, optimizing the design of these assays with potentially hundreds of prototype targets exceeds what is possible by current methods. To address these issues, a computationally efficient model for predicting base calling for resequencing microarrays was successfully developed that begin with a simple assumption to predict hybridization and then only added complexity as needed. A large set of data for organism and short oligonucleotide hybridization and base calling with Affymetrix CustomSeq microarrays allowed testing and validation of the model.

Disclosed is a model applicable to resequencing microarrays that predicts the base calls that will occur for a sample sequence on a specified prototype sequence of the microarray. A "prototype" sequence is the designation for the genomic sequence used to generate the probe sets placed on the resequencing array allowing at least partial hybridization of a selected range of pathogen target sequences. Although rules similar to those used in designing for other arrays are the starting point to allow rapid calculations, more detailed thermodynamic information is incorporated. The model development is facilitated by testing against a large set of data for organisms and short oligonucleotide hybridizations and base calling on Affymetrix resequencing microarrays. The model is successful at predicting base calls from hybridization of a large variety of target organism sequences. It can further be used to predict how well prototype sequences represented on the microarray will perform against a diverse set of pathogen targets. This will assist in simplifying the design of resequencing microarrays and reduce the time and costs required for their development for specific applications.

Model Concept—Experimentally, a probe set will only indicate that a specific base is present if a fragment binds better to one probe of the set. To model this behavior, the central assumption made is that when a probe and a sample sequence have in contiguous bases that complement, an observable hybridization signal occurs. This is the roughest approximation to represent the difference in binding strengths of different sequences to a probe and represents the simplest model. The remainder of the modeling consists of generating probes from the prototype sequence and potential binding fragments from the sample, and then comparing the sets with each other using the central assumption.

The first step is to generate the probe sets and sample fragments. A sequence selected to be the prototype sequence is divided into overlapping sets of 4 probes, where the probes of a set are each, for example, 25 bases long and differ at the central base (i.e. for a sequence of L bases, L-24 probe sets are produced). This represents what may actually be located on a microarray. For a sample sequence, all unique fragments that are in bases long are generated (i.e. for a sequence of K bases, at most K−m+1 unique fragments can be produced). Fragments in an experiment may be longer than this (average of 100 bases). The model only requires that the minimum requirement of m bases be present in a fragment.

Now that the microarray probes and sample fragments have been generated, each probe of every probe set is tested against all the fragments from the sample sequence to determine if a perfect complement match occurs. Probes having a match are noted. The ability of a probe set to produce a base call is evaluated by considering the results of its probes. If only one probe of the set has a match in the sample sequence, that is the base call assigned for the probe set and the next probe set is examined. N, representing an ambiguous base identity, is assigned when none of the sample fragments are a match to any member of the probe set. In the case that more than one probes of a set has a match, longer fragments are generated from the sample sequence and then compared. The neighboring bases of each fragment in the 5'-3' direction from the sample sequence are added to one at a time until a mismatch occurs with the appropriate probe. If one of these fragments is now longer than the others, then that base is assigned, otherwise N is assigned.

After all probe sets are tested, the base calls (A, C, T, G, or N) from each probe set are reassembled into a sequence. FIG. 1 shows example results of the model using different values of m from 23 to 13 (lengths less than 13 were not used as they can bind nonspecifically, though it is possible to use them) and points out some base calls made under various conditions. Although experimental results clearly indicate it is not necessary for a fragment to complement all 25 or even 21 bases of a probe to produce a specific base call. Without further experimental input, it is difficult to determine what length for m is most appropriate.

Short Oligomers—A large amount of data on the hybridization of short oligonucleotides was available from Respiratory Pathogen Microarray v.1 (RPMv.1) (Lin et al. (2006) Broad-spectrum respiratory tract pathogen identification using resequencing DNA microarrays. *Genome Res,* 16, 527-535) experiments using a multiplex of specific primers for sample amplification. Since unused primers were not removed from the sample before hybridization and most of these primers were within the prototype sequences, it is possible to study the binding of a large number of short oligomers 16 to 27 bases in length to resequencing microarrays. The data sets are for two multiplex mixtures, one contains 117 primers (777 experiments) and the other (906 experiments) consists of 66 primers that are a subset of the 117-primer mixture. There are multiple probe sets available from the prototype sequence that will hybridize with the same primer but have a different number of bases that exactly match available for hybridizing (from 13 bases to the length of the primer or the length of the probe, 25 bases). For example, the base at either end of the primer oligomer has a probe set that may determine the identity of the base but only based on hybridization of 13 bases. The primers of any prototype sequence that showed better than 50 percent hybridization for its entire sequence were not included in the analysis as they represent hybridization of unused primer and primer incorporated into amplicons of the target. From the collection of primer oligomers available there were ~$3 \times 10^5$ data points for each length from 13 to 21, ~$2 \times 10^5$ for 22, ~$1.5 \times 10^5$ for 23 and ~$7.5 \times 10^4$ for each length of 24 and 25. Base calling was preformed by GDAS program settings used in previous work (Lin et al. (2006) Broad-spectrum respiratory tract pathogen identification using resequencing DNA microarrays. *Genome Res,* 16, 527-535).

FIG. 2 shows the frequency of an unambiguous base call versus the amount of primer that can hybridize to a probe for all primers and two groups of primers based on their GC content. The first position has a frequency of 33% which indicates that 1 time in 3 a DNA fragment that only matches 13 of the 25 bases in a probe is able to bind specifically and strongly enough to generate a unique base call. As the length of bases available to hybridize increases, an increasing frequency of base calling is observed and reaches 50% or more by a length of 16. To further understand the binding frequency, the results of the multiplex primers hybridization were divided into two groups based on their GC content. The averages for primers are shown grouped with GC contents less than 50% and greater than or equal to 50%. This division places roughly twice the number of samples in the lower bracket than are in the upper bracket for lengths up to 22. The difference in frequency of base calling is largest going from 13 to 14. The rates and trend from 23 to 25 for GC content greater than 50% has greater uncertainty, as there are significantly fewer probe samples in these brackets.

Figure 3:
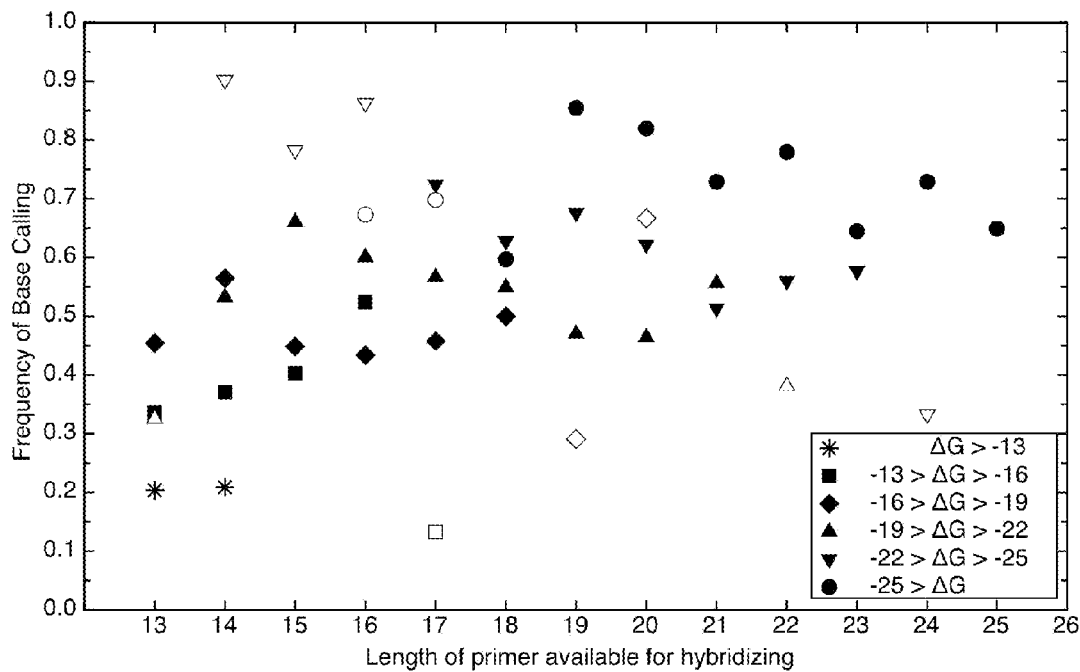
FIG. 3 shows the frequency of resolved base calls from primers as a function of position within the primer. ΔG (open symbols indicate bin with fewer than 12000 data points): *>−13, −13>■☐>−16, −16>◆◇>−19, −19>▲△>−22, −22>▼▽>−25, −25>●○

To understand the influence of primer composition better, FIG. 3 shows the primers of each length in separate groups based on the $\Delta G$ calculated by the nn model (SantaLucia (1998) A unified view of polymer, dumbbell, and oligonucleotide DNA nearest-neighbor thermodynamics. *Proc. Natl. Acad. Sci. USA*, 95, 1460-1465; SantaLucia et al. (2004) The thermodynamics of DNA structural motifs. *Annu. Rev. Biophys. Biomol. Struct.*, 33, 415-440). Some of these bins have very few samples and those results exhibit greater uncertainty. Nevertheless, a trend can be observed that overall as the $\Delta G$ decreases, the frequency increases irrespective of the length. The interesting point is using one perfect match and three mismatch probes a high base call frequency is possible for oligomer lengths significantly shorter than the length of the probes (25 bases). The only probes that clearly have a low frequency of making base call on the array have lengths of 13 and 14 and $\Delta G$ greater than $-13$ kcal/mol. Primers with $\Delta G$ lower than $-16$ kcal/mol on average have 50 percent or greater chance to hybridize and produce a base call.

Revised Model Concept—The experimental evidence from the trend in the binding frequencies indicates that lengths longer than 16 are likely to frequently generate a resolved base call without considering any other factors. For shorter lengths, the $\Delta G$ of the probe is important in determining if there will be a significant chance of resolving base call. The model was modified to determine the $\Delta G$ of the fragments generated from the sample with m=13. If the fragment's free energy difference is below the cutoff, $-14.5$ kcal/mol, it is accepted. In the case it is above the cutoff, the length of the fragment is increased until its energy is below the cutoff or it reaches the length of a probe, 25. The resulting list of fragments is then compared against every probe set as already mentioned.

Amplification, hybridization, and sequence determination—The details of the Respiratory Pathogen Microarray v.1 (RPM v.1) design and the experimental methods have been discussed in previous work (Wang et al. (2006) Identifying Influenza Viruses with Resequencing Microarrays. *Emerg Infect Dis*, 12, 638-646; Lin et al. (2006) Broad-spectrum respiratory tract pathogen identification using resequencing DNA microarrays. *Genome Res*, 16, 527-535; Davignon et al. (2005) Use of resequencing oligonucleotide microarrays for identification of *Streptococcus* pyogenes and associated antibiotic resistance determinants. *J Clin Microbiol*, 43, 5690-5695; Lin et al. (2007) Using a Resequencing Microarray as a Multiple Respiratory Pathogen Detection Assay. *J Clin Microbiol.*, 45(2), 443-452). Partial sequences from the genes containing diagnostic regions were tiled for the detection of these pathogens. The experimental microarray data used for the initial primer analysis were obtained from clinical samples using multiplexed RT-PCR amplification schemes. The results for test of primer results and the California lineage samples used a different multiplex protocol (Lin et al. (2007) *J Clin Microbiol.*, 45(2), 443-452). The remaining influenza samples used a random protocol (Wang et al. (2006) *Emerg Infect Dis*, 12, 638-646). GCOS™ software v1.3 (Affymetrix Inc., Santa Clara, Calif.) was used to determine the intensities of the probes and the base calls were made using GDAS v3.0.2.8 software (Affymetrix Inc., Santa Clara, Calif.).

Case 1: Predicting Primer Interference—The first test use of the model algorithm was to understand base calling that was occurring in 42 microarray experiments with a blank sample (no nucleic acids added) using a new primer set that tried to minimize the primer interaction with the prototype sequences. Since the primers were still present, they were treated as collection of sample sequences and tested using the model against every prototype sequence on the chip. The model accurately predicted the base calling occurring in the experiments from primers that were still located on the prototype sequences. Additional binding to locations in the center of prototype sequences was also seen and agreed with the experimental results. Primers designed for prototype sequences of closely related organisms caused these base calls. For example, the adenovirus 4 E1A gene prototype sequence has 19 of 20 predicted bases being called 97% of the time, which is located 393 bases from the beginning of the sequence. One base, which is a single nucleotide polymorphism (SNP) at the edge of the region, was predicted to call was but was observed only called 12% of the time in the experiments. This region when compared to other prototype sequences is a match for primer region selected for the adenovirus 7 E1A prototype region. Similar agreement was seen for the other 47 regions predicted by the model.

Case 2: Model Predictions for Long Sequences—After successful demonstration of the accuracy of the model for shorter fragments, the predictions for entire prototype sequences were examined. Results using conventional sequencing samples in the model compared to experimental microarray results for four data sets; influenza A/H3N2 Fujian-like lineage, influenza A/H3N2 California-like lineage, influenza B Yamagata/16/88 lineage, and influenza B Victoria/2/87 are reported in Table 1. The results report averages for samples that have a great deal of similarity such as for the influenza A/H3N2 Fujian-like samples, the average base call rate for the experiments was 85% while the model predictions averaged 97%. The average number of SNPs was 9.8 (1%) between the prototype and the conventional sequences. While the model predicted 9.2 SNPs would be resolved, only 6.3 SNPs were observed in the experiments. The model predicts 8.8 N calls that the experiment has a specific base call, and the microarray has 94.9 N calls that the model predicts should be a specific base call. So on average 14.3 N calls match between model and microarray results.

TABLE 1

Summary of average model and experimental microarray results for influenza hemagglutinin gene that could be placed in separate groups based on lineage.

| Sample Set Influenza | Tile | Resolved Base calls | | Number SNPs with respect to Prototype | | | Number N calls | | |
|---|---|---|---|---|---|---|---|---|---|
| | | Array | Model | Conv | Model | Array | Model only | Array only | Model and Array |
| A Fujian-like lineage (12) | 770 | 85.4 ± 3.6 | 96.7 ± 0.012 | 9.8 | 9.2 | 9.2 (0)* | 8.8 | 94.9 | 14.6 |
| A California-like lineage (12) | 770 | 92.2 ± 7.8 | 95.3 ± 0.013 | 11.9 | 11.6 | 10.7 (1)* | 15.3 | 38.7 | 21.5 |
| B Yamagata lineage (8) | 660 | 77.5 ± 3.7 | 86.8 ± 0.011 | 24.5 | 17.6 | 12.2 (1)* | 26.4 | 87.2 | 61 |
| B Victoria Lineage (4) | 660 | 47.7 ± 3.9 | 51.4 ± 0.007 | 65.2 | 39.2 | 31.2 (4)* | 70.2 | 94.2 | 251 |

*numbers in parentheses are number of disagreements with respect to conventional results Table 2 shows for a specific isolate from the Fujian-like lineage samples (identified as A/Nepal/1727/2004) the location of each of 6 SNPs resolved on the microarray and the number of additional bases that were called N in a 25 base long window centered on the SNPs. The total base call rates were 97.4% for the model and 88.4% for the microarray. Using this information to group the N calls, 46 N calls are closely related with SNPs and 29 N calls are spread uniformly across the microarray and mostly consisted of single N calls surrounded by resolved bases or a few events of two consecutive N calls or two N calls in a group of three bases. The sample has a total of 8 SNPs when comparing the conventional and prototype sequences and the two SNPs not identified on the microarray were both located near other SNPs that were identified. The model and microarray agree on 12 N calls located near 7 different SNPs but six more N calls predicted in the model near SNPs were resolved in the experiment and so represent discrepancies in the model.

TABLE 2

Location of SNP for influenza A strain compared to FluAHA3 prototype sequence.

| Location | Target Base | Actual Base | N calls in local region(chip) | N calls in local region (model) |
|---|---|---|---|---|
| 299 | G | A | 10 | 1 |
| 313 | G | A | 8 | 1 |
| 352 | A | C | 10 | 8 |
| 393 | A | T | 2 | 3 |
| 483 | G | A | 5 | 0 |
| 593 | G | A | 8 | 3 |
| 596 | T | C | 8 | 3 |
| 698 | C | A | 3 | 4 |

The prototype sequence differed from the sample sequence by 1.5% for the influenza A/H3N2 California-like lineage samples and 3.7% for the influenza B Yamagata/16/88 lineage samples and 9.8% for the influenza B Victoria/2/87 lineage samples. These results differed from the first group of samples also in that there were disagreements between the conventional sequencing and the microarray base calls other than N calls. The influenza B samples that were run under the same protocol as the influenza A/H3N2 Fujian-like lineage had 1 (Yamagata lineage) and 4 (Victoria lineage) base call differences. These bases calls all occurred in regions at least 3 N calls from any regions of many resolved base calls and the model predicted N base calls at these locations. The influenza A/H3N2 California-like samples used a different protocol and while the disagreements have many N calls near them, they do not consistently have at least 3 N calls separating them from regions of many resolved bases. This accuracy of 99.87% on the bases calls is a reasonable error rate to expect when determining the base calls from a single microarray experiment.

Figure 4:
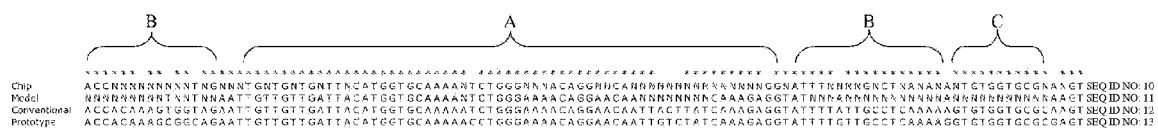
FIG. 4 shows the prototype sequence of FluBHA and results for an influenza B Victoria lineage sample from conventional sequencing, from RPMv.1 microarray, and from model prediction. Region A represents a section sequence where SNPs are very far apart or close together and the model and microarray data agree well. Region B sequences have SNPs with an intermediate frequency and the agreement between model and experiment decreases. This behavior observed as the percent difference between sample and prototype sequence rises above 4%. Region C is similar although the number of observed base calls observed is much higher and these cases were only observed at 10%.

The model has a similar performance for the percentage of base calls predicted for samples that differ from the prototype sequence from 1% to 4% and appears to have a slightly better agreement when the difference increase to ~10%. However, overall base call percentage can be a misleading indicator of model performance. The N calls can be broken down into three groups; N calls predicted in model but not observed, N calls observed but not predicted, and N calls both predicted and observed. Examining the trends one can see that for the three sample sets subject to the same protocol as the amount of variation increased from 1% to 10%, the predicted N calls that matched observed N calls increased by the largest amount reflecting where the model is accurate. The N calls observed but not predicted remains roughly constant. The N calls made in the model but that are resolved base calls on the chip also increases. The improved agreement for the percentage of base calls seen at 10% is caused by the increase overall base call. Overall the other influenza A/H3N2 sample behaves in a similar manner to the other data sets and the differences in some details probably reflect differences in the protocol used. Even though the model is not as accurate when SNPs occur more frequently, the regions that have a lower frequency are correctly identified and these are the regions that are used in our current pathogen identification analysis. FIG. 4 shows a section from an influenza B sample that differs by 10%. Some features like the large stretches of N calls or resolved calls are present in all sample sets. The stretches of base calls from these regions are what are used most often in the analysis program, CIBSI v.2. The B regions of FIG. 4 represent scattered base calls in a region of predicted N calls and are found in the sample sets having 4% or more variation. The C region in FIG. 4 is similar to region B except in this case many more experimentally resolved base calls in the region are predicted as N. This type of behavior was only observed in the samples of 10% variation.

The model can be used to understand the behavior of an organism when using a representative sequence from a genomic sequence database rather than the conventional sequencing of the sample. An example is the influenza A/Puerto Rico/8/34 strain was used as a spike in test on the microarray and the experiments only had significant base call rates on the neuraminidase and matrix prototype sequences. This is consistent with the model simulation which correctly identified the regions in the two prototype sequences that would generate significant base calls and predicted that an insignificant number of base calls would occur in the hemagglutinin prototype sequence due to differences between the influenza A/Puerto Rico/8/34 strain and prototype sequence.

The examination of a large collection of resequencing microarray probe sets using well defined short oligomer probes has clearly demonstrated that short fragments with only 16 sequential complementary bases can produce accurate base discrimination a significant fraction of the time. This hybridization is independent of GC content or calculated $\Delta G$, and segments as short as 13 bases will produce calls when the GC content or $\Delta G$ is favorable. The simple model for predicting hybridization patterns developed in this study has excellent agreement with observed experimental results when it was assumed that only 13 contiguous bases matching perfectly are required for specific binding. Better agreement was reached by also requiring that the predicted size of $\Delta G$ of a binding fragment meet a minimal size requirement. The implication for resequencing microarrays is that significant amounts of specific hybridization occurs, with resultant nucleotide base calling, for fragments that have less than a perfect 25 base match with the probes. The testing of the primers demonstrated the difficulties in eliminating all potential cross-hybridization of primers with prototype sequences in highly multiplexed systems. However, because probe-target hybridization on the microarray can be predicted, it is straightforward to account for cross-hybridization effects when analyzing the results and does not need to be physically eliminated. The model performs reasonably well, particularly for the application that drove its development and has provided insight into why this detection method works in complex mixtures. It should be applicable for predicting behavior of other microarrays that use complete match-mismatch probe sets with different criteria to select the probe sets, such as Affymetrix Mapping Arrays and Genotyping Arrays.

When considering the influenza B samples, it becomes apparent that some fragments that could potentially bind to probes might be missed when 13 contiguous complementary bases are required for hybridization. The evidence also suggests that fragments containing one mismatch with sufficiently strong binding energy can result in base calls. Unfortunately, the few samples of influenza B currently available make it impractical to try to establish what energy a fragment must have when it contains a mismatch. Another shortcoming of the model relates to its failure to predict N calls that are not closely associated with a SNP. Experimental microarray results provide only one microarray result per sample. Thus, it cannot be determined whether the scattered N calls appear reproducibly or randomly as many factors might influence this behavior. The formation of self-loop structures was eliminated as a dominant factor in the model, since incorporation of this did not result in matching prediction and observed experimental patterns.

The current model can be used to predict whether sufficient base calls will occur for a pathogen of interest within a selected prototype sequence to be identified using the analysis program, CIBSI V2.0 (Malanoski et al. (2006) Automated identification of multiple micro-organisms from resequencing DNA microarrays. *Nucleic Acids Res.*, 34, 5300-5311). A simple rule of thumb can be made that sequences that differ by more than 80 percent from the probe sequence have few instances in which sufficient matching bases are contiguous to allow a significant amount of base calling and will never generate organism identification by our methods. This is a useful quick estimate of the upper bound on the maximum number of reference strains a probe sequence can detect. The developed model can be applied to the sequences that fall within this range to more accurately predict which organisms can be detected and the performance of a prototype sequence.

The results of the modeling can be used for selection of the prototypes for inclusion on a microarray. The overall design process can be implemented in the next microarray designs for biothreat agents and a regional (e.g. Africa) organisms specific microarray. The identification of the regions from organisms may or may not be solely a literature search. This will remain an important tool for larger genome targets but may be unnecessary for viral organisms with smaller genomes. The methodology for organism detection that will be applicable for any design can be characterized as a series of steps. First, the list of sequences is to include target sequences and any sequences from near genetic neighbors so that the effect of their hybridization to the reference sequences can be checked. A gross predictor of hybridization can be obtained from the percentage of bases that match an alignment procedure (BLAST). By using cutoff criteria below the percentage that commonly gives the smallest usable hybridization program, it is possible from BLAST queries to construct a list of sequences that may potentially hybridize in different regions. This list of sequences is to include target sequences and any sequences from near genetic neighbors so that the effect of their hybridization to the reference sequences can be checked. Second, coupling sequence selection with taxonomic information each region can be evaluated for whether it can give the desired level of discrimination and whether it limits its detection to desired targets only or not. This will provides an immediate upper limit on the possible number of organisms a reference sequence may usefully detect. Third, after the best candidate regions are determined using the above methods. Fourth, a list of the number of strains each strain can detect is made and used as the criteria for selecting reference strains. Fifth, the strain that detects the most other strains is removed from the list and used as the first reference strain. All strains that it is capable of detecting are also removed from the list. Of the remaining strains, the one that detects the most other strains is selected as the next reference strain. In the general formulation rather than limiting comparison to sequences only with the target, each of the sequences that need to be detected is tested as a potential reference sequence. The other organism sequences it can potentially identify will be obtained from a query using BLAST to determine which subset of the sequences has a chance of hybridizing. This subset is simulated with the more detailed model to predict hybridization. The resulting hybridization is evaluated using the detection algorithm developed to classify hybridization on real chips rather then the simpler criteria used before. For each potential reference sequence, a refined upper bound on the number of target and non-target sequences each can detect can now be established. Selection of reference sequences used will then proceed in a manner to use the minimum space to provide the required level of discrimination. Primer selection is then performed after the sequences have been selected.

The method may have the following features. The method does not rely on open literature solely to determine the reference sequences selection as they may be outdated from the addition of new organism sequence since the publication. The design scheme provides an independent check on the validity of the reference sequences selected before fabrication is carried out. The may be improvement over selected reference sequences which were possible only between microarrays designs based upon the performance of previous chip design.

The method may determine a smaller set of reference sequences that can provide the level of discrimination specified without prior validation. The method may allow for an automation process for target gene selections and shorten the turn around time for chip design.

Having described the invention, the following examples are given to illustrate specific applications of the invention. These specific examples are not intended to limit the scope of the invention described in this application.

EXAMPLE 1

Hypothetical example with short sequences—The following illustrates the disclosed methods using artificial, short sequences not intended to correspond to any particular real species. It is desired to fabricate a resequencing microarray for detection of species A, B, C, D, and E. As used herein, "species" may refer to taxonomic species as well as different types or strains of a single species, and combinations thereof. It is known that nominal target 1 (FIG. 5) is found in the genome of at least one of these species. A search for similar sequences is performed using a database such as BLAST to produce a list of targets. A minimum percent similarity, for example 70%, may be used to filter the results. If too many targets or targets from too many species, such as genetically distant species, are reported, the percentage may be raised to reduce the size of the list. Also, the list may be manually reviewed for removal of specific, undesirable targets.

FIG. 5 shows a hypothetical list of targets 10-40. (Reference number ranges such as "10-40" include only numbers of that form, rather than every number from 10 to 40.) The list of targets is provided to a computer system, which may be the same computer used to create the list. The list and all subsequently described data in this example at least up to assembling base call sequences is stored in a computer memory or medium. The list of candidate prototype sequences 100-400 in this example is identical to the list of targets 10-40, though that is not required.

FIG. 6 shows a hypothetical collection of probes 111-434 derived from the candidate prototype sequences 100-400. The subsequence length of the probes is chosen to be seven, though other values maybe used. Probes 111-134 are derived from candidate prototype 100, and so forth. Probe 111 is the first seven bases of candidate prototype 100. Probes 112-114 are single nucleotide polymorphisms of probe 111 at the center position. Probes 111-114 make up one set of probes. Probes 121 and 131 are also seven base subsequences of candidate prototype 100, each shifting one base to the right. Thus, all three possible seven base subsequences of candidate prototype 100 are in the collection of probes. Probes 122-124 and 132-134 are single nucleotide polymorphisms of probes 121 and 131, respectively.

FIG. 7 shows a hypothetical list of fragments 11-46 derived from the targets 10-40. The fragment length is chosen to be 4, though other values may be used. Thus a target with a length of nine has six possible fragments. Also shown is a list of extended fragments 11'-46', containing some original fragments and some fragments made by adding extra bases from the target. The extended fragments are made by calculating the binding free energy of each fragment with a perfect complimentary sequence of the fragment. If the binding free energy for a fragment is above a predetermined, fixed threshold, the fragment is extended one nucleotide at a time until the binding free energy is below the threshold or the fragment is the same length as the probe. One suitable method of calculating the binding free energy is an oligonucleotide nearest neighbor model, though other methods may be used. A suitable binding free energy threshold for use with Affymetrix resequencing arrays is about −14.5 kcal/mol, though other values may be used. (No actual calculation was performed for this example, as it is illustrative.)

FIG. 8 shows all perfect matches between the probes and the extended fragments. The probe sets starting with 111, 131, 211, 221, 231, 321, 411, and 421 contain only one probe that matches any extended fragments. When assembling a base call sequence, these sets produce a base call that is the same as the center base of the first (non-polymorph) probe of the set. The probe sets starting with 121, 311, 331, and 431 contain more than one probe that matches any extended fragments. A non-base call ("N") is assigned for these probe sets. If there were any probe sets with no matches, these would also be assigned a non-base call. The base call sequence for each candidate prototype sequence and the probe sets from which they are derived are shown in FIG. 9.

FIG. 10 shows the lists of matching organisms for each candidate prototype. The checked organisms contain the corresponding candidate prototype. This may be determined by reference to external databases. The minimum number of base calls is chosen to be 2, though larger numbers, such as 50, may be used. As such, no list of matching organisms need be made for candidate prototype 300, as its base call sequence (NGN) contains only one base call. This is the case even if it would match the most organisms. Candidate prototype 400 matches the most organisms (A, B, and E). It is added to the list of final prototypes and removed from the list of candidate prototypes. A, B, and E are removed from the list of organisms. At this point candidate prototype 100 matches two of the remaining organisms (C and D) while candidate prototype 200 matches only one (C). Candidate prototype 100 is added to the list of final prototypes and removed from the list of candidate prototypes. C and D are removed from the list of organisms. As the list of organisms is now empty, no more prototypes are moved to the list of final prototypes.

A resequencing microarray may be fabricated containing each set of probes corresponding to each final prototype sequence. Here the microarray would contain probes 111, 112, 113, 114, 121, 122, 123, 124, 131, 132, 133, 134, 411, 412, 413, 414, 421, 422, 423, 424, 431, 432, 433, and 434. This set of probes will detect each organism even though it does not detect every target. The microarray may also contain a sequence complimentary to each of these probes.

This example is based on a single nominal target, but more than one nominal target may be used. The target sequences may correspond to a single gene in common to a subset of the organisms, and the list of organisms may comprise a plurality of strains of a single species. If the resulting list of final prototypes cannot detect all the organisms, then the process or parts thereof may be repeated with different parameters, such as targets, candidate prototypes, probe length, fragment length, and minimum number of base calls.

EXAMPLE 2

Enteroviruses and Adenoviruses—The process was performed using enteroviruses and adenoviruses as the list of organisms. The final prototypes sequences are identified as SEQ ID NOS: 14-51. A resequencing microarray containing the probe sets generated from these prototypes was made has been designated RPMv.3.

Obviously, many modifications and variations of the present invention are possible in light of the above teachings. It is therefore to be understood that the claimed invention may be practiced otherwise than as specifically described. Any reference to claim elements in the singular, e.g., using the articles "a," "an," "the," or "said" is not construed as limiting the element to the singular.

What is claimed is:

1. A computer-implemented method comprising:

providing a list of target sequences associated with one or more organisms in a list of organisms;

providing a list of candidate prototype sequences suspected of hybridizing to one or more of the target sequences;

generating a collection of probes corresponding to each candidate prototype sequence, each collection of probes comprising a set of probes for every subsequence having a predetermined, fixed subsequence length of the corresponding candidate prototype sequence, the set consisting of the corresponding subsequence and every variation of the corresponding subsequence formed by varying a center nucleotide of the corresponding subsequence;

generating a set of fragments corresponding to each target sequence, each set of fragments comprising every fragment having a predetermined, fixed fragment length of the corresponding target sequence;

calculating the binding free energy of each fragment with a perfect complementary sequence of the fragment, and if any binding free energy is above a predetermined, fixed threshold, the fragment is extended one nucleotide at a time until the binding free energy is below the threshold or the fragment is the same length as the probes corresponding to the corresponding target sequence, generating a set of extended fragments; and determining which extended fragments are perfect matches to any of the probes; and assembling a base call sequence corresponding to each candidate prototype sequence comprising:

a base call corresponding to the center nucleotide of each probe of the corresponding prototype sequence that is a perfect match to any extended fragment, but for which the other members of the set of probes containing the perfect match probe are not perfect matches to any extended fragment; and a non-base call in all other circumstances;

wherein the method is at least partly performed using a suitably programmed computer.

2. The method of claim 1, wherein a subset of the target sequences corresponds to a single gene in common to a subset of the organisms.

3. The method of claim 1, wherein the list of organisms comprises a plurality of strains of a single species.

4. The method of claim 1, further comprising:

selecting a nominal target sequence known to be found in at least one of the organisms; and performing a similarity search against a database of known sequences to add additional target sequences having at least a predetermined degree of similarity to the nominal target sequence;

wherein the list of candidate prototype sequences is identical to the list of target sequences.

5. The method of claim 1, wherein the subsequence length is 25.

6. The method of claim 1, wherein the fragment length is 13.

7. The method of claim 1, wherein the binding free energy is calculated according to an oligonucleotide nearest neighbor model.

8. The method of claim 1, wherein the binding free energy threshold is about −14.5 kcal/mol.

9. The method of claim 1, further comprising:

generating for each candidate prototype sequence a list of matching organisms containing that candidate prototype sequence for which the base call sequence corresponding to that candidate prototype sequence comprises a fixed minimum number of base calls;

moving the candidate prototype sequence corresponding to the longest list of matching organisms to a list of final prototype sequences;

removing the matching organisms corresponding to the moved prototype sequence from the list of organisms; and repeating the moving and removing until the list of organisms is empty.

10. The method of claim 9, wherein the minimum number of base calls is 50.

11. The method of claim 9, further comprising:

fabricating a resequencing microarray containing each set of probes corresponding to each final prototype sequence.

12. The method of claim 11, wherein the microarray further comprises a sequence complementary to each probe on the microarray.

* * * * *